US007727994B2

(12) United States Patent
Kase et al.

(10) Patent No.: US 7,727,994 B2
(45) Date of Patent: *Jun. 1, 2010

(54) METHODS OF TREATING PATIENTS SUFFERING FROM MOVEMENT DISORDERS

(75) Inventors: Hiroshi Kase, Tokyo (JP); Akihisa Mori, Chiba (JP); Yutaka Waki, Princeton, NJ (US); Yutaka Ohsawa, London (GB); Akira Karasawa, Shizuoka (JP); Yoshihisa Kuwana, Shizuoka (JP)

(73) Assignee: Kyowa Hakko Kirin Co., Ltd., Tokyo (JP)

( * ) Notice: Subject to any disclaimer, the term of this patent is extended or adjusted under 35 U.S.C. 154(b) by 233 days.

This patent is subject to a terminal disclaimer.

(21) Appl. No.: 11/326,516

(22) Filed: Jan. 6, 2006

(65) Prior Publication Data
US 2006/0148827 A1 Jul. 6, 2006

Related U.S. Application Data

(62) Division of application No. 10/353,240, filed on Jan. 28, 2003.

(51) Int. Cl.
*A61K 31/522* (2006.01)
*A61K 31/505* (2006.01)
(52) U.S. Cl. .................. 514/263.34; 514/267
(58) Field of Classification Search ............ 514/263.34, 514/267, 253.34
See application file for complete search history.

(56) References Cited

U.S. PATENT DOCUMENTS

| 5,484,920 | A | 1/1996 | Suzuki et al. |
| 5,543,415 | A | 8/1996 | Suzuki et al. |
| 5,587,378 | A | 12/1996 | Suzuki et al. |
| 6,608,085 | B1 | 8/2003 | Gillespie et al. |
| 6,787,541 | B1 | 9/2004 | Gillespie et al. |

FOREIGN PATENT DOCUMENTS

| EP | 1 016 407 | 7/2000 |
| WO | WO 02/055524 | 7/2002 |
| WO | WO 02/080957 | 10/2002 |

OTHER PUBLICATIONS

Konda et al., "Adenosine A2a Antagonist: A Novel Antiparkisonian Agent that Does Not Provoke Dyskinesia in Parkinsonian Monkeys", Annals of Neurology, vol. 43, No. 4, pp. 507-513 (1998).*
Grondin et al., "Antiparkinsonian effect of a new selective adenosine A2a receptor antagonist in MPTP-treated monkeys", Neurology, vol. 52, pp. 1673-1677 (1999).*
Hashimoto ("Pathophysiology of Abnormal Movements in Parkinson's Disease", Nippon Rinsho, Oct. 2000, 58(1): 1994-1999; Abstract Only).*
Kanda, et al., "Combined Use of the Adenosine $A_{2A}$ Antagonist KW-6002 with L-DOPA or with Selective D1 or D2 . . .", *Experimental Neurology*, vol. 162 (2000), pp. 321-327.
Rashad Net University, Parkinson's Disease: Update, pp. 1-14, www.rashaduniversity.com/mrashad/padiup.html (2005).
Sundstrom, et al., "Chronic neurochemical and behavioral changes in MPTP-lesioned . . .", Brain Research, vol. 528 (1990) 181-88.
Fredriksson, et al., "Synergistic interactions between NMDA-antagonists and L-Dopa on activity in MPTP-treated mice", J. Neural Transm, vol. 97 (1994) 197-209.
Ossowska, et al., "Blockage of the metabotropic glutamate receptor subtype 5 (mGluR5) products . . .", Neuropharmacology, vol. 41 (2001) 413-20.
Ungerstedt, "Postsynaptic Supersensitivity after 6-Hydroxydopamine Induced Degeneration . . .", Acta Physio. Scand., vol. 367 (1971) 69-93.
Spooren, et al., "Effects of the prototypical mGlu5 receptor antagonist . . .", European Journal of Pharmacology, vol. 406 (2000) 403-10.
Cardoso, et al., "Dystonia and Dyskinesia", Neuropsychiatry of the Basal Ganglia, vol. 20, No. 4 (1997) 821-38.
Diaz-Cabiale, et al, "Adenosine A2A agonist CGS 21680 decreases the affinity of dopamine D2 receptors for dopamine in human striatum", Neurochemistry, vol. 12, No. 9 (2001) 1831-34.
Ferre, et al, "Adenosine/dopamine interaction: implications for the treatment of Parkinson's disease", Parkinsonism and Related Disorders, vol. 7 (2001) 235-41.
Webster Ross, et al., "Association of Coffee and Caffeine Intake With the Risk of Parkinson Disease", JAMA, vol. 283, No. 20 (2000) 2674-79.

(Continued)

*Primary Examiner*—Kevin Weddington
(74) *Attorney, Agent, or Firm*—Fitzpatrick, Cella, Harper & Scinto

(57) ABSTRACT

The present invention is directed to methods of treating movement disorders by administering an effective amount of one or more adenosine $A_{2A}$ receptor antagonists to a patient in need thereof. The present invention also provides methods of decreasing the adverse effects of L-DOPA in patients receiving L-DOPA therapy in the treatment of Parkinson's disease. The present invention further provides methods and compositions for treating Parkinson's disease patients with subclinically effective doses of L-DOPA by combining L-DOPA treatment with an effective amount of one or more adenosine $A_{2A}$ receptor antagonists (i.e., L-DOPA sparing effect). The present invention further provides methods of effective treatment of Parkinson's disease by co-administering at least one adenosine $A_{2A}$ receptor antagonist, L-DOPA and a dopamine agonist and/or a COMT inhibitor and/or a MAO inhibitor. The present invention further provides methods of prolonging effective treatment of Parkinson's disease by administering an adenosine $A_{2A}$ receptor antagonist singly or together with a dopamine agonist, and/or a COMT inhibitor, and/or a MAO inhibitor without prior or subsequent administration of L-DOPA, delaying or removing on-set of L-DOPA motor complication.

3 Claims, 11 Drawing Sheets

OTHER PUBLICATIONS

Popoli, et al., "Effects of SCH 58261, an Adenosine A2A Receptor Antagonist, on Quinpirole-Induced Turning in 6-Hydroxydopamine-Lesioned Rats: Lack of Tolerance after Chronic Caffeine Intake", Neuropyschopharmacology, vol. 22, No. 5 (2000) 522-29.

Koga, et al., "Adenosine A2A receptor antagonists KF17837 and KW-6002 potentiate rotation induced by dopaminergic drugs in hemi-Parkinsonian rats", European Journal of Pharmacology, vol. 408 (2000) 249-55.

Shiozaki, et al, "Actions of adenosine A2A receptor antagonist KW-6002 on drug-induced catalepsy and hypokinesia caused by reserpine or MPTP", Psychopharmacology, vol. 147 (1999) 90-5.

Kanda, et al., "Adenosine A2A receptors modify motor function in MPTP-treated common marmosets", Neuropharmacology, vol. 9, No. 12 (1998) 2857-60.

Ferre, et al, "Adenosine-dopamine receptor-receptor interactions as an integrative mechanisms in the basal ganglia", TINS, vol. 20, No. 10 (1997) 482-87.

Richardson, et al, "Adenosine A2A receptor antagonists as new agents for the treatment of Parkinson's disease", TiPS, vol. 18 (1997) 338-44.

Fenu, et al., "Adenosine A2A receptor antagonism potentiates L-DOPA-induced turning behaviour and c-fos expression in 6-hydroxydopamine-lesioned", European Journal of Pharmacology, vol. 321 (1997) 143-47.

Pinna, et al., "Blockage of A2A Adenosine Receptors Positively Modulates Turning Behaviour and c-Fos Expression Induced by D1 Agonists in Dopamine-denervated Rats", European Journal of Neurosciences, vol. 8, No. 6 (1996) 1176-81.

Mally, et al., "Potential Role of Adenosine Antagonist Therapy in Pathological Tremor Disorders", Pharmacol. Ther., vol. 72, No. 3 (1996) 243-50.

Pollack, et al., "Adenosine Antagonists Potentiate D2 Dopamine-Dependent Activation of Fos in the Striatopallidal Pathway", Neurosciences, vol. 68, No. 3 (1995) 721-28.

Mally, et al., "The effect of theophylline on parkinsonian symptoms", J. Pharm. Pharmacol., vol. 46, No. 6 (1994) 515-17.

Kanda, et al., "KF17837: a novel selective adenosine A2A receptor antagonist with anticataleptic activity", European Journal of Pharmacology, vol. 256 (1994) 263-68.

Schiffmann, et al., "Adenosine A2 Receptors Regulate the Gene Expression of Striatopallidal and Striatonigral Neurons", The Journal of Neurosciences, vol. 13, No. 3 (1993) 1080-87.

Ferre, et al., "Stimulation of high-affinity adenosine A2 receptors decreases the affinity of dopamine D2 receptors in rat striatal membranes", Proc. Natl. Acad. Sci., vol. 88 (1991) 7238-41.

Popoli, et al., "Akinesia due to catecholamine depletion in mice is prevented by caffeine. Further evidence for an involvement of adenosinergic system in the control of motility", J. Pharm. Pharmacol., vol. 43, No. 4 (1991) 280-81.

Stromberg, et al., "Further Studies on the Behavioural and Biochemical Interaction between Caffein and L-DOPA", Journal of Neural Transmission, vol. 34, No. 4 (1973) 241-52.

Grondin, et al., "Antiparkinsonian effect of a new selective adenosine A2A receptor antagonist in MPTP-treated monkeys", Neurology, vol. 52, No. 8 (1999) 1673-77.

Kanda, et al., "Adenosine A2A Antagonist: A Novel Antiparkinsonian Agent that Does Not Provoke Dyskinesia in Parkinsonian Monkeys", Ann Neurol, vol. 43, No. 4 (1998), 507-13.

* cited by examiner

FIGURE 5A (upper), and 5B (lower)
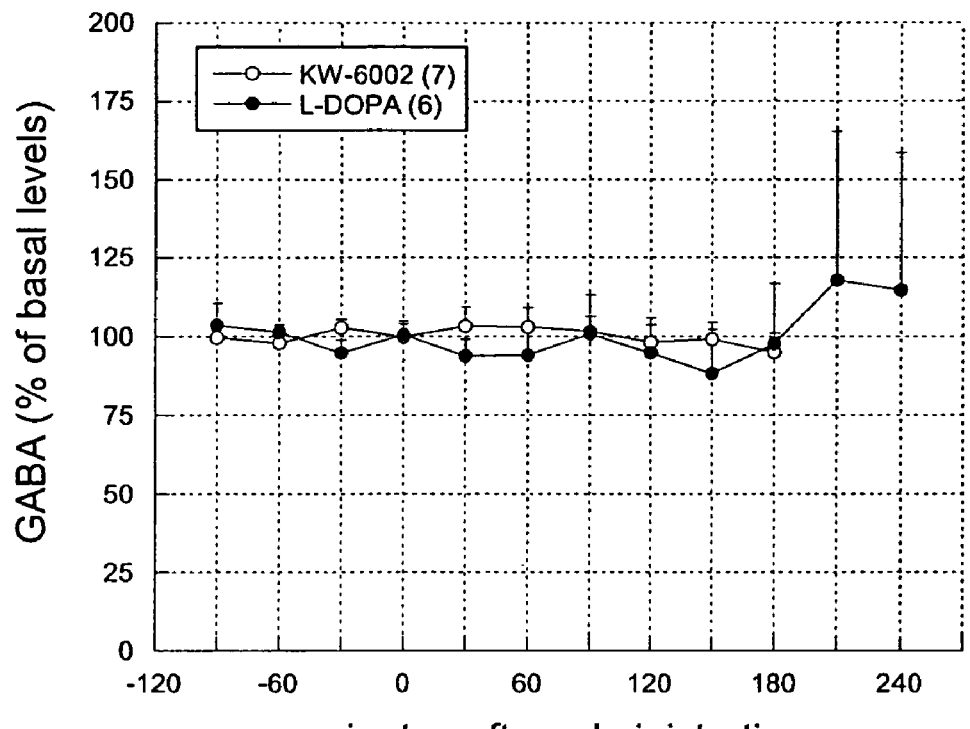
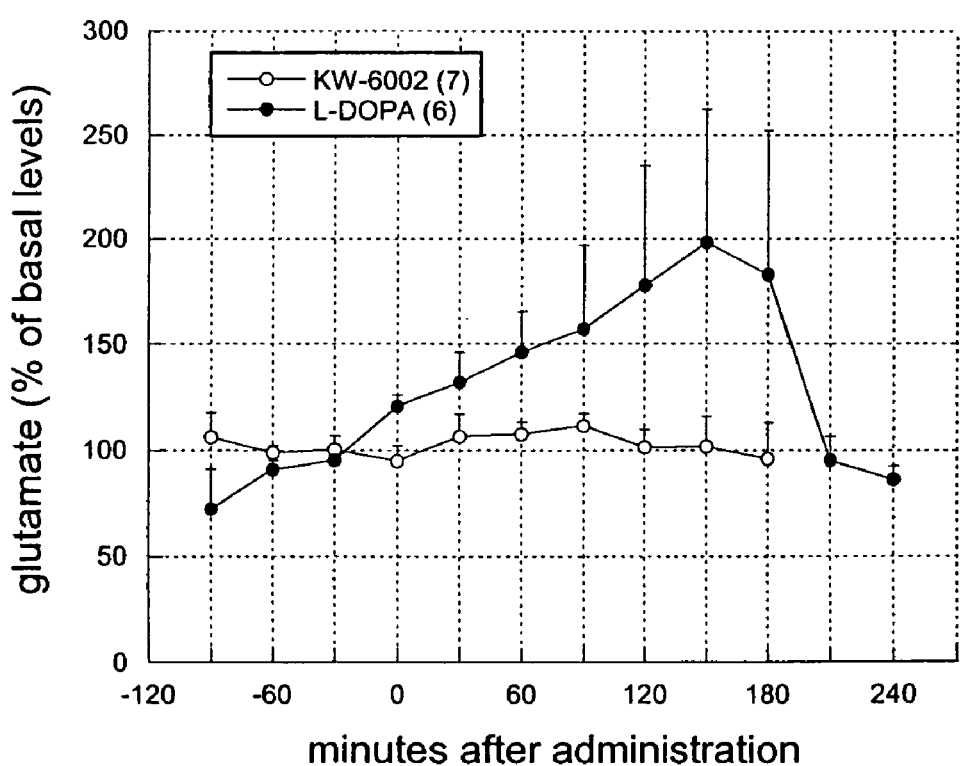

Each column represents the mean (±SEM) of the maximal dyskinesia score (Max dyskinesia score) for 8 animals. #P<0.05 compared with vehicle control *P<0.05 compared with L-DOPA pre (10 mg/kg). +P<0.05 compared with L-DOPA control (2.5 mg/kg).

METHODS OF TREATING PATIENTS SUFFERING FROM MOVEMENT DISORDERS

This application is a divisional of application Ser. No. 10/353,240 filed Jan. 28, 2003.

FIELD OF THE INVENTION

The present invention is directed to methods of treating patients suffering from movement disorders comprising administering at least one adenosine $A_{2A}$ receptor antagonist.

BACKGROUND OF THE INVENTION

Movement Disorders are neurological conditions characterized by either a paucity or lack of movement (such as Parkinson disease) or excessive movement (such as dystonia, dyskinesia, tremor, chorea, ballism, akathisia, athetosis, bradykinesia, freezing, rigidity, postural instability, myoclonus, and tics or Tourette syndrome). See, Watts and William eds. (1997); and Shulman and Weiner (1997).

Parkinson's Disease and Motor Complication

Parkinson's disease (paralysis agitans) is a disorder of the brain characterized by shaking and difficulty with walking, movement, and coordination. The disease is associated with damage to a part of the brain that controls muscle movement.

Parkinson's disease was first described in England in 1817 by James Parkinson. The disease affects approximately 2 out of 1,000 people, and most often develops after age 50. The symptoms first appear, on average, at about age 60, and the severity of Parkinson's symptoms tends to worsen over time. It affects both men and women and is one of the most common neurologic disorders of the elderly. The term "parkinsonism" refers to any condition that involves a combination of the types of changes in movement seen in Parkinson's disease. Parkinsonism may be genetic, or caused by other disorders or by external factors (secondary parkinsonism).

In the United States, about a million people are believed to suffer from Parkinson's disease, and about 50,000 new cases are reported every year. Because the symptoms typically appear later in life, these figures are expected to grow as the average age of the population increases over the next several decades. The disorder is most frequent among people in their 70s and 80s, and appears to be slightly more common in men than in women.

The dopaminergic neurons of the substantia nigra pars compacta and ventral tegmental area play a crucial role in regulating movement and cognition, respectively. Several lines of evidence suggest that the degeneration of dopaminergic cells (i.e. dopamine-producing cells) in the substantia nigra produces the symptoms of Parkinson's disease. Dopaminergic cells, concentrated in the region of the substantia nigra, are the fastest aging cells in the body. As dopaminergic cells decay, control over movement is diminished and Parkinson's disease develops.

Usually the first symptom of Parkinson's disease is tremor (trembling or shaking) of a limb, especially when the body is at rest. The tremor often begins on one side of the body, frequently in one hand. Other common symptoms include other movement disorders such as slow movement (bradykinesia), an inability to move (akinesia), rigid limbs, a shuffling gait, and a stooped posture. Parkinson's disease patients often show reduced facial expression and speak in a soft voice. The disease can cause secondary symptoms of depression, anxiety, personality changes, cognitive impairment, dementia, sleep disturbances, speech impairments or sexual difficulties.

There is no known cure for Parkinson's disease. Treatment is aimed at controlling the symptoms. Medications control symptoms primarily by controlling the imbalance between the neurotransmitters. Most early Parkinson's disease patients respond well to symptomatic treatment with dopamine replacement therapy, but disability increases with progression of the disease.

The medications used, the dose and the amount of time between doses vary, depending on the case. The combination of medications used may need to be adjusted as symptoms change. Many of the medications can cause severe side effects, so monitoring and follow-up by the health care provider is important.

Although currently available medications for Parkinson's disease generally provide adequate symptomatic control for a number of years, many patients develop motor fluctuations and dyskinesias that compromise clinical response. Rascol et al. (2000); and Parkinson Study Group (2000). Once this occurs, increasing dopaminergic therapy is likely to worsen dyskinesias and decreasing dopaminergic therapy is likely to worsen motor function and increase OFF time. In light of this problem, attention has turned to potential therapeutic manipulation of non-dopaminergic neurotransmitter systems.

Most Parkinson's disease symptoms arise from a deficiency of dopamine and most anti-Parkinson drugs restore dopamine or mimic dopamine's actions. However, the drugs do not permanently restore dopamine or exactly mimic dopamine's actions. While a loss of dopamine cells in the substantia nigra is the main feature of Parkinson's disease, non-dopamine nerve cells are also lost. Moreover, dopamine-responsive cells are present not only in the substantia nigra but in other brain regions. Thus drugs that are effective in Parkinson's disease can, by stimulating these cells, cause side effects such as nausea, hallucinations, and confusion.

In 1967, L-DOPA was introduced and remains the most effective anti-Parkinson drug. Symptoms most likely to benefit from L-DOPA include bradykinesia, rigidity, resting tremor, difficulty walking, and micrographia. Symptoms least likely to benefit from L-DOPA include postural instability, action tremor, and difficulty swallowing. L-DOPA may worsen dementia. Although L-DOPA provides robust and rapid therapeutic benefits in Parkinson's disease, eventually, severe adverse reactions to dopamine emerge, including motor complications such as wearing off phenomenon, ON-OFF fluctuations, and dyskinesia. Marsden et al. (1982). Once established, motor complications are not typically controllable with manipulation of L-DOPA or other dopaminergic drugs.

Early in Parkinson's disease L-DOPA is taken 3 times per day. Peak concentrations in the brain occur 1 to 2 hours after administrations. Although the drug has a short half-life (0.5 to 1 hour) there are sufficient remaining dopamine cells in the brain to store dopamine and maintain its activity over several hours. As Parkinson's disease progresses, more dopamine cells die and the remaining cells cannot store sufficient dopamine to maintain its benefits: the duration of action of each dose decreases and patients need higher or more frequent doses. After 2-5 years as many as 50-75% of patients experience fluctuations in their response to L-DOPA: ON/OFF periods. Associated with the fluctuations, patients develop dyskinesias. The dyskinesias usually occur at the peak effect of L-DOPA but can also occur as the drug wears off, or at stressful times. The fluctuations and dyskinesias can seriously impact the patient's life. If L-DOPA is given continuously (through an intravenous pump) ON/OFF effects disappear and dyskinesias decrease. However, it is impractical to give L-DOPA intravenously.

When L-DOPA is taken alone part of it is changed outside the brain to dopamine by dopa-decarboxylase. The dopamine so produced cannot enter the brain and causes side effects such as nausea, vomiting, and appetite loss. Therefore L-DOPA is often combined with carbidopa or benserazide. Carbidopa blocks dopa-decarboxylase outside the brain allowing more L-DOPA to enter the brain without causing nausea, vomiting, and appetite loss. Atamet or Sinemet are tablets containing both carbidopa and L-DOPA. In combination with carbidopa, the half-life of L-DOPA is 1.2 to 2.3 hours.

Thirty years after its discovery, L-DOPA is still the best treatment for Parkinson's disease. In the early stages of the disease, patients usually enjoy a good response to L-DOPA, but as the disease progresses L-DOPA-tends to become less helpful. This is not due to loss of L-DOPA efficacy, but rather to development of motor complications such as adverse fluctuations in motor response including end-of-dose deterioration or "wearing-off", and the "ON/OFF" fluctuations and dyskinesias. ON/OFF fluctuations are a sudden, unacceptable loss of therapeutic benefit of a medication ('ON' state, during which the patient is relatively free from the symptoms of Parkinson's disease) and onset of the parkinsonian state ('OFF' state). Wearing off phenomenon is a decrease in the duration of L-DOPA action, and characterized by the gradual reappearance of the 'off' state, and shortening the 'on' state. Dyskinesia can be broadly classified as chorea (hyperkinetic, purposeless dance-like movements) and dystonia (sustained, abnormal muscle contractions). In 1974, Duvoisin first focused on these abnormal involuntary movements, and found that over half of patients with Parkinson's disease developed dyskinesia within six months of treatment. With increasing duration of treatment, there is an increase in both the frequency and severity of dyskinesia. In a seminal study of the potential benefits of possible neuroprotectants in Parkinson's disease—the DATATOP trial-L-DOPA induced dyskinesia was observed in 20-30% of patients who received L-DOPA treatment for a mean of 20.5 months. Ultimately, most L-DOPA treated patients experienced dyskinesia; up to 80% of patients developed dyskinesia within five years of treatment. Parkinson Study Group (1996); and Rascol et al. (2000). Treatment-related dyskinesias are not solely a problem of L-DOPA, as dopamine receptor agonists are also capable of eliciting dyskinesia. Thus, the common term "L-DOPA-induced dyskinesia" could be used to describe dopamine-treatment-related dyskinesia in general terms. Most dyskinesias occur when levodopa or other dopamine receptor agonists have a concentration in the brain that is sufficient to overactive dopamine receptors in the putamen (peak-dose-dyskinesia). However, dyskinesia also occurs when dopamine concentration is low (OFF dystonia) or in stages when the concentration of dopamine rises or falls (biphasic dyskinesia). Other movement disorders, such as myoclonus and akathisia, might also be components of the L-DOPA induced dyskinesia spectrum.

The biological basis of L-DOPA motor complications in Parkinson's disease is still far from clear. It has been suggested that they may involve not only advancing disease and continued loss of nigral neurons, but also changes of dopamine receptor sensitivity and their downstream expression of proteins, and genes, the sequence of events of which relate, at least in part, to the dose and method of administration of L-DOPA or dopamine agonists. Changes in non dopamine systems such as glutamate-mediated neurotransmission, GABA-mediated neurotransmission, and opioid peptide mediated transmission, might also be involved in the neuronal mechanisms that underlie L-DOPA motor complications in Parkinson's disease. Bezard et al. (2001). Notably, it seems that the short plasma half-life and consequent short duration of action of dopaminergic agents and the pulsatile stimulation of dopamine receptors by dopaminergic agents are associated with motor fluctuations and peak-dose-dyskinesias. All these events combine to produce alterations in the firing patterns that signal between the basal ganglia and the cortex.

Originally introduced as adjunctive therapy to L-DOPA in patients with fluctuations, dopamine agonists are now increasingly proposed as monotherapy in early patients. The antiparkinsonian effects of dopamine agonists, however, are usually less than those of L-DOPA, and after two to four years their efficacy wanes. When more potent treatment is required, low doses of L-DOPA can be "added on" to the agonist. An alternative strategy is to combine an agonist with low doses of L-DOPA from the beginning. Both strategies are purported to be as effective as L-DOPA and to have the advantage of significantly reducing the risk of motor fluctuations and dyskinesias. These claims, however, are based upon a small number of pilot studies, all of which suffer from methodological shortcomings.

Additionally, dopamine receptor agonists are also capable of eliciting dyskinesia. Dopamine agonists also provoke dyskinesia in parkinsonian animals previously exposed by L-DOPA. Neuropsychiatric side effects, especially hallucination and psychosis, often limit the use of dopamine agonists. Despite the potential benefits provided by the adjunctive use of dopamine agonists, L-DOPA motor complications can thus be extremely difficult or even impossible to control. See, Olanow, Watts and Koller eds. (2001). Finally, dopamine agonists are sometimes used in monotherapy as substitutes for L-DOPA in patients with advanced Parkinson's disease and severe motor fluctuations and dyskinesias.

More recently, catecholamine-O-methyltransferase (COMT) inhibitors such as tolcapone and entacapone have been proposed as adjunctive therapy to L-DOPA. These compounds extend the plasma half-life of L-DOPA, without significantly increasing $C_{max}$. Thus, they decrease the duration of wearing-off but tend to increase the intensity of peak-dose side effects including peak-dose-dyskinesias. Tolcapone appears to induce significant liver toxicity in a small percentage of patients.

Anti-cholinergics such as tri-hexiphenidyl (Artane) and piperidine (Cogentin) block the actions of acetylcholine in the brain. This may result in a mild to moderate degree of improvement in symptoms such as drooling and tremor. Patients above age 65 are likely to experience side effects such as dry mouth, blurred vision, constipation, confusion and hallucinations when treated with anti-cholinergics.

Dystonias

The term dystonia refers to a movement disorder characterized by sustained muscle contractions resulting in a persistently abnormal posture. Based on this definition, there are a number of dystonic syndromes, which can be subdivided according to their clinical features as: generalized (affecting all body parts); segmental (affecting adjacent body parts); or focal (restricted to a single body part). Focal dystonias include spasmodic torticollis, blepharospasm, hemifacial spasm, oromandibular dystonia, spasmodic dysphonia, and dystonic writer's cramp.

There are several degrees of dystonia. Some people can maintain a relatively normal life-style, while others are permanently hindered, often needing full time assistance.

Symptoms may be focal or limited to one region of the body, such as the neck or an arm or a leg. There are many different types of focal dystonia. Blepharospasm is marked by involuntary contraction of the muscles that control the movement of the eyelids. Symptoms may range from intermittent, painless, increased blinking to constant, painful, eye closure leading to functional blindness. In patients with cervical dystonia (CD), also known as spasmodic torticollis, muscle spasms of the head and neck may be painful and cause the neck to twist. These sometimes painful spasms may be intermittent or constant. Oromandibular and lingual dystonia is characterized by forceful contractions of the lower face causing the mouth to open or close. Chewing and unusual tongue movements may also occur. In spasmodic dysphonia (SD), also known as laryngeal dystonia, the muscles in the voice box (larynx) are affected. SD is marked by difficulties either opening or closing the vocal cords, causing the voice to have either a strained, hoarse, strangled, or whispering quality. In limb dystonia, there are involuntary contractions of one or more muscles in the arm, hand, leg, or foot. These types of focal dystonias include writer's cramp and other occupational dystonias.

Some patients have symptoms that are segmental or involve two adjacent areas of the body, such as the head and neck or arm and trunk. In other patients, symptoms may be multifocal or appear in two areas of the body that are not next to each other, such as the two arms, or an arm and a leg. In generalized dystonia, symptoms begin in an arm or a leg and advance, becoming more widespread. Eventually, the trunk and the rest of the body are involved.

Most cases of primary or idiopathic dystonia are believed to be hereditary and occur as the result of a faulty gene(s). In these patients, dystonia occurs as a solitary symptom and is not associated with an underlying disorder. For example, most cases of early-onset primary dystonia are due to a mutation in the DYT-1 gene. Early-onset dystonia that occurs as a result of this disease gene is the most common and severe type of hereditary dystonia. Other genetic causes of primary dystonia are rare.

Diseases involving dystonias include hereditary spastic paraplegia (HSP), a group of genetic, degenerative disorders of the spinal cord characterized by progressive weakness and stiffness of the legs; Huntington's disease (HD) a hereditary progressive neurodegenerative disorder characterized by the development of emotional, behavioral, and psychiatric abnormalities and movement abnormalities; multiple system atrophy (MSA) a neurodegenerative disease marked by a combination of symptoms affecting movement, blood pressure, and other body functions; pathologic myoclonus; progressive supranuclear palsy; restless legs syndrome; Rett syndrome; spasticity; Sydenham's chorea; Tourette syndrome; and Wilson disease.

Dystonia may occur because of another underlying disease process such as Wilson disease, multiple sclerosis, stroke, etc.; trauma to the brain, such as injury during a vehicular accident or anoxia during birth; or as a side effect of a medication. This type of dystonia is termed secondary or symptomatic dystonia. In adults, the most common type of secondary dystonia is tardive dystonia, which occurs as a result of the use of certain neuroleptic or antipsychotic drugs (used to treat psychiatric disorders). These drugs include haloperidol (Haldol®) or chlorpromazine (Thorazine®). Other drugs that block central dopamine receptors may also cause tardive dystonia. In most patients, symptoms occur some time after ongoing exposure to the drug. Table 1 provides a list of drugs that can cause dystonia.

TABLE 1

| Generic | (Trade Names) |
|---|---|
| Acetophenazine | (Tindal ®) |
| Amoxapine | (Asendin ®) |
| Chlorpromazine | (Thorazine ®) |
| Fluphenazine | (Permitil ®, Prolixin ®) |
| Haloperidol | (Haldol ®) |
| Loxapine | (Loxitane ®, Daxolin ®) |
| Mesoridazine | (Serentil ®) |
| Metaclopramide | (Reglan ®) |
| Molindone | (Lindone ®, Moban ®) |
| Perphenazine | (Trilafon ® or Triavil ®) |
| Piperacetazine | (Quide ®) |
| Prochlorperazine | (Compazine ®, Combid ®) |
| Promazine | (Sparine ®) |
| Promethazine | (Phenergan ®) |
| Thiethylperazine | (Torecan ®) |
| Thioridazine | (Mellaril ®) |
| Thiothixene | (Navane ®) |
| Trifluoperazine | (Stelazine ®) |
| Triflupromazine | (Vesprin ®) |
| Trimeprazine | (Temaril ®) |

There are a number of options available to treat dystonia. Drugs may be used alone or in combination. In addition, they may be combined with other forms of treatment. Drugs currently in use include botulinum toxin (BTX), benzodiazepines, Baclofen, anticholinergics and dopamine-blocking agents/dopamine-depleting agents. Surgical treatment is also available and includes thalamotomy, pallidotomy, deep brain stimulation, myectomy (myotomy), ramisectomy, rhizotomy and peripheral denervation.

Tardive Dyskinesia and other Extrapyramidal Syndromes

The extrapyramidal system of the nervous system is centered on the basal ganglia and influences motor control through pyramidal pathways, generally by means of input to the thalamus. When the extrapyramidal system is disturbed, motor control is affected and patients suffer extrapyramidal syndromes. These are a combination of neurological effects that include tremors, chorea, athetosis, and dystonia. This is a common side effect of neuroleptic agents. Other medications known to cause these reactions include haloperidol, molindone, perphenazine and aminotriptyline, loxapine, pimozide, and rarely, benzodiazepines.

Tardive dyskinesia is an involuntary neurological movement disorder. Depending upon the type of onset, a differential diagnosis might include Sydenham's chorea, Huntington's chorea, congenital torsion dystonia, hysteria, and the stereotyped behavior or mannerism of schizophrenia. American College of Neuropsychopharmacology-FDA Task Force (1973). Tardive dyskinesia results from the use of neuroleptic drugs that are prescribed to treat certain psychiatric or gastrointestinal conditions. Long-term use of these drugs may produce biochemical abnormalities in the striatum. Tardive dystonia is believed to be the more severe form of tardive dyskinesia.

Other closely related, untreatable neurological disorders have now been recognized as variants of tardive dyskinesia. Tardive akathisia involves painful feelings of inner tension and anxiety and a compulsive drive to move the body. In the extreme, the individual undergoes internal torture and can no longer sit still. Tardive dystonia involves muscle spasms, frequently of the face, neck and shoulders, and it too can be disfiguring, disabling and agonizing.

Treatment of tardive dyskinesia has been unsatisfactory. Removal of the antipsychotic agent is often advocated (Baldessarini (1990)) but often results in more severe forms of the movement disorder. Various pharmaceutical agents have been tried with some reported success; early investigators in this area turned their attention to reserpine (Serpasil®), tradename of Ciba-Geigy a compound known to deplete dopamine levels. Reserpine and α-methyldopa (Aldomet®) in the treatment of long-standing tardive dyskinesia showed that both compounds were statistically more effective than placebo in reducing symptomatology. Huang et al. (1981). However, another study showed that, catecholamine synthesis blockers such as α-methyldopa have not demonstrated a beneficial effect on tardive dyskinesia. AMPT, an experimental agent that inhibits tyrosine hydroxylase, the rate-limiting step in the synthesis of dopamine and norepinephrine, has shown partial reduction of dyskinesia.

Formerly, tardive dyskinesia was often treated by increasing the dose of the neuroleptic. This initially treats the pathophysiology of tardive dyskinesia but can aggravate the pathogenesis by further denervation and subsequent hypersensitivity. Thus, the movements may decrease or disappear initially but then reappear later. The use of the atypical neuroleptic, clozapine may be useful in certain situations in which patients with disfiguring tardive dyskinesia need neuroleptic treatment alternative.

Lithium interferes with the presynaptic release of monoamines as well as having other actions on the CNS. Two studies report mild improvement in tardive dyskinesia with lithium while two others report no improvement or exacerbation. Tepper and Haas (1979).

Oral pimozide caused improvement in degree of movement. Clayeria et al. (1975). Buspirone (BuSpar®), a partial serotonin receptor agonist, may also be useful in treating the condition. Moss et al. (1993). In rats, buspirone reverses the DA receptor subsensitivity induced by chronic neuroleptic administration, and it is this effect that may also occur in humans due to partial agonist effects at D2 receptors. Reports have associated tardive dyskinesia with reserpine, tetrabenazine, metoclopramide, tricyclic antidepressants, benztropine, phenyloin and amphetamines.

Other than neuroleptics, the drug that regularly produces dyskinesia is L-DOPA and other dopaminergic agents, in patients receiving these drugs for Parkinson's diseases. L-DOPA actually can improve neuroleptic-induced tardive dyskinesia.

There is no accepted treatment for tardive dyskinesia. Casey (1999). Either discontinuing the offending antipsychotic or switching a patient to an atypical antipsychotic (with the possible exception of risperidone) may alleviate the movement disorder. The treatment of tardive dyskinesia has been recently reviewed. Egan et al. (1997). Most pharmacologic treatment strategies are directed toward reducing dopamine activity or enhancing CNS cholinergic effect. If the etiology of tardive dyskinesia relates to chronic dopaminergic receptor site blockade and the pathophysiology relates to the denervation hypersensitivity, agents that interrupt this sequence would, theoretically, be of potential benefit.

Many drugs have been tried in treating neuroleptic-induced tardive dyskinesia. Because of differences in patient populations, study design, and doses of agents used, the results for individual agents are conflicting. Baldessarini and Tarsy (1978); and Klawans et al. (1980).

Amine depleting agents e.g., reserpine and tetrabenazine, act by blocking the reuptake of dopamine, norepinephrine, and serotonin into the presynaptic neuronal storage vesicles, thereby depleting the brain of these substances. Studies with these agents have indicated improvement in tardive dyskinesia but side effects have limited their use and the studies are of short duration. Short-term suppression may occur as reported with neuroleptics.

Several cholinergic agonists have been administered to patients with tardive dyskinesia. Choline chloride and phosphatidylcholine (lecithin), which are orally bioavailable precursors of acetylcholine, have been reported to be useful in short-term studies. Deanol acetaminobenzoate was originally reported to be efficacious in the treatment of tardive dyskinesia, but other studies have not confirmed these findings. Gelenberg et al. (1990).

There have been several attempts to treat tardive dyskinesia with drugs believed to potentiate central GABA mechanisms. Thaker et al. (1990). In a study involving 10 patients with tardive dyskinesia of greater than a 6 month duration, benztropine 2 mg IV increased dyskinetic movements in 7 patients and reduced them in the remaining three. Moore and Bowers (1980). In a preliminary report the β-adrenergic blocking agent propranolol (Inderal®) in a dose of 30-60 mg/day produced marked resolution of tardive dyskinesia within 1 to 10 days of treatment in four patients. Wilbur and Kulik (1980).

Several studies have examined the effectiveness of treating tardive dyskinesia with vitamin E. Adler et al. (1999); Lohr and Caligiuri (1996); Lohr et al. (1988); Elkashef et al. (1990); Shriqui et al. (1992); Egan et al. (1992); Adler et al. (1993a); Adler et al. (1993b); Goldberg (1996); McCreadie et al. (1994); Dabiri et al. (1993); Bischot et al. (1993); Akhtar et al. (1993); and Dabiri et al. (1994).

It was previously thought that in the majority of patients, tardive dyskinesia is permanent or irreversible. However, this is not necessarily the case. The earlier tardive dyskinesia is diagnosed and the neuroleptic discontinued, the better the prognosis for disorder reversal. In young adults, tardive dyskinesia disappears within several weeks after early drug withdrawal. Uhrbrand and Faurbye (1960); Itoh et al. (1981); Driesens (1988); and Gardos et al. (1994).

Table 2 summarizes various agents that have been used to treat tardive dyskinesia.

TABLE 2

| Classes of Agents | Specific agents |
|---|---|
| Dopamine antagonists | Butyrophenones, clozapine, metoclopramide (Karp et al. (1981)), papaverine (mechanism uncertain), phenothiazines, bromocriptine, pimozide |
| Dopamine D2 Agonists | Buspirone |
| Amine-depleting agents | Reserpine, tetrabenzine |
| Blocker of catecholamine synthesis | α-methyldopa, α-methyltyrosine (AMPT) |
| Catecholamine release blocker | Lithium salts |
| Cholinergic agents | Deanol, physostigmine, choline and lecithin |
| GABA agonists | Progabide (Bartholini (1983)), valproic acid, baclofen, iazepam, clonazepam |

TABLE 2-continued

| Classes of Agents | Specific agents |
| --- | --- |
| Anticholinergic agents. Moore et al. (1980) | Benztropine, trihexyphenidyl |
| Agents with variable, negligible, or uncertain effects | α-methyldopa, amantadine, anticholinergics antihistamines, apomorphine, barbiturates, benzodiazepines, methylphenidate, penicillamine, physostigmine, pyridoxine (B6), tryptophan, α-tocopherol (Vitamin E) |
| Agents that worsen tardive dyskinesia | Anticholinergic agents, antiparkinson agents (e.g., benztropine), dopamine agonists, amphetamines, L-DOPA |
| Newer investigational agents (peptides). Blurn et al. (1983) | endopioids, Substance P, Cholecystokinin, Ceruletide, Neurotensin, Cyclo-Leucine-Glycine |

Other motor syndromes caused by the effects of neuroleptic drugs on the extrapyramidal system include drug induced parkinsonism, akathisia, dystonia, oculogyric crisis, and opisthotonus. Akathisia is a condition that is characterized by motor restlessness, which may range from anxiety to an inability to lie or sit quietly, or to sleep, and possible causes include a toxic reaction to neuroleptics such as phenothiazine. An oculogyric crisis is the paroxysmal, involuntary upward deviation of the eyes. The eyelids are often retracted. Attacks last from a few minutes to a few hours. It may occur in patients sensitive to phenothiazines, haloperidol, and metoclopramide. Opisthotonus is a form of spasm in which head, neck and spine are arched backwards Adenosine $A_{2A}$ Receptors Adenosine is known to act via four major receptor subtypes, $A_1$, $A_{2A}$, $A_{2B}$, $A_3$, which have been characterized according to their primary sequences. Fredholm et al. (1994). Adenosine $A_2$ receptors are further divided into $A_{2A}$ (high-affinity) and $A_{2B}$ (low-affinity) subtypes. Daly et al. (1983); and Burns et al. (1986). In contrast to the widespread distribution of $A_1$, $A_{2B}$, and $A_3$ receptors in the brain, $A_{2A}$ receptors are highly localized to the basal ganglia, especially to the caudate-putamen (striatum), nucleus accumbens and globus pallidal, and the olfactory tubercles. Jarvis et al. (1989); and Schiffmann (1991b). The basal ganglia are located in the telencephalon and consist of several interconnected nuclei: the striatum, globus pallidus external segment (GPe), globus pallidus internal segment (GPi), substantia nigra pars compacta (SNc), substantia nigra pars reticulata (SNr), and subthalamic nucleus (STN). The basal ganglia are a critical component of subcortical circuits involved in the integration of sensorimotor, associative, and limbic information to produce motor behavior. A major component of basal ganglia is the striatum, where GABAergic medium spiny neurons, which represent more than 90% of striatal neuronal population, are the only projection neurons.

The medium spiny neurons receive massive glutamatergic inputs from the cortex and thalamus, and project their GABAergic output onto the major output nuclei of basal ganglia, i.e. GPi and SNr, via the striatopallidal medium spiny neurons in an "indirect pathway" and the striatonigral medium spiny neurons in a "direct pathway." Alexander et al. (1990); Gerfen (1992); and Graybiel (1990). The medium spiny neurons also receive intrastriatal GABAergic, cholinergic, and nigrostriatal dopaminergic modulatory inputs. Neurons of the striatonigral direct pathway contain GABA plus substance P/dynorphin and directly project from the striatum to GPi/SNr. These neurons provide a direct inhibitory effect on GPi/SNr neurons. Striatal neurons in the striatopallidal indirect pathway contain GABA plus enkephalin and connect the striatum with the GPi/SNr via synaptic connections in the GPe and STN. In these neurons, $A_{2A}$ receptors are located almost exclusively on striatopallidal medium spiny neurons in the striatum and globus pallidus of the indirect pathway [Schiffmann et al. (1991a)], and acetylcholine-containing large aspiny interneurons in the striatum [Dixon et al. (1996)], and have been shown to modulate the neurotransmission of GABA, acetylcholine and glutamate. Kurokawa et al. (1996); Mori et al. (1996); Shindou et al. (2001); Ochi et al. (2000); Richardson et al. (1997); and Kase (2001).

Recent advances in neuroscience together with development of selective agents for the $A_{2A}$ receptors have contributed to increased knowledge about adenosine and the adenosine $A_{2A}$ receptor. Behavioral studies show that adenosine $A_{2A}$ receptor antagonists improve motor dysfunction of several parkinsonian animal models (e.g., MPTP-treated monkeys), but also reveal features of $A_{2A}$ receptor antagonists distinctive from dopaminergic agents. Richardson et al. (1997); Kase et al. (2000); and Kase (2001).

The antiparkinsonian effects of the selective adenosine $A_{2A}$ receptor antagonist KW-6002 have been studied in MPTP-treated marmosets and cynomologus monkeys. Kanda et al. (1998a); Grondin et al. (1999); and Kanda et al. (2000). In MPTP-treated marmosets, oral administration of KW-6002 induced an increase in locomotor activity lasting up to 11 hours in a dose-related manner. Kanda et al. (1998a). Locomotor activity was increased to the level observed in normal animals whereas L-DOPA induced locomotor hyperactivity. Furthermore, in L-DOPA-primed MPTP-treated marmosets, treatment with KW-6002 for 21 days induced little or no dyskinesias whereas under the same conditions, treatment with L-DOPA induced marked dyskinesias. When KW-6002 (20 mg/kg) was administered once a day for 5 days with a threshold dose of L-DOPA to MPTP-treated marmosets primed to exhibit dyskinesias, antiparkinson activity was potentiated without an increase in dyskinesia. Kanda et al. (2000). KW-6002 also additively increased the antiparkinsonian effect of quinpirole, a dopamine D2 receptor agonist but not SKF80723, a dopamine D1 receptor agonist. Taken together, these findings suggest that adenosine $A_{2A}$ antagonists might provide antiparkinsonian benefit as monotherapy in patients with early Parkinson's disease and might be able to improve antiparkinsonian response without increasing dyskinesia in L-DOPA-treated patients with motor complications.

Although the mechanisms by which adenosine $A_{2A}$ antagonists exert an antiparkinsonian effect remain to be fully elucidated, the following mechanism is now proposed.

In either Parkinson's disease or MPTP treatment of primates, following destruction of the nigro-striatal dopaminergic pathway, the most relevant alteration is hyperactivity in the striatopallidal pathway, and such hyperactivity is attributed to an imbalance between the direct striatonigral pathway and the indirect striatopallidal pathway to give rise to parkinsonian state. DeLong (1990); and Obeso et al. (2000). It is noted that $A_{2A}$ receptors are specifically expressed on a subpopulation of medium spiny neurons, the striatopallidal medium spiny neurons but not the striatonigral medium spiny neurons.

The GABAergic striatopallidal medium spiny projection neuron was found as one of major target neurons of $A_{2A}$ receptor-mediated modulation. Kase (2001). Thus, in the striatum, $A_{2A}$ receptors control excitability of the projection neurons through the intrastriatal GABAergic feedback/feedforward inhibition network [Mori et al (1996)], and in the globus pallidus (GPe), $A_{2A}$ receptor activation enhances GABA release from the nerve terminals and might suppress excitability of GPe projection neurons, which project to subthalamus nucleus (STN) [Shindou et al. (2001)]. $A_{2A}$ receptor antagonists selectively block the dual modulation mechanism in the striatopallidal system, leading to suppression of the excessive activation in the striatopallidal medium spiny neurons. This might shift the striatopallidal/striatonigral neuronal imbalance towards the normal state, resulting in recovery of the motor function in parkinsonean state. Ochi et al (2000); Kase (2001), Aoyama et al (2002).

The action mechanism via $A_{2A}$ receptors could work independently of dopamine $D_2$ receptors (Aoyama et al. (2000)), which are co-localized with $A_{2A}$ receptors in the striatopallidal medium spiny neurons. Gerfen et al. (1990). $D_2$ receptor knockout mice ($D_2R-/-$) presented a locomotor phenotype with analogies to Parkinson's disease and significantly altered in the levels of neuropeptide genes expressed in the striatal medium spiny neurons. No difference in the distribution and level of expression of $A_{2A}$ receptor mRNA and the binding properties of the receptor were found between $D_2R-/-$ and wild type mice, indicating that $D_2$ receptor absence had no influence on $A_{2A}$ receptor properties. Blockade of $A_{2A}$ receptors by KW-6002 reestablished their locomotor activity and coordination of movement and lowered the levels of striatal enkephalin expression to those in normal mice. Aoyama et al. (2000). The results indicate that $A_{2A}$ and $D_2$ receptors have antagonistic but independent activities in controlling neuronal and motor function in the basal ganglia. Independent functioning of $A_{2A}$ receptors from the dopaminergic system was confirmed by studies using $A_{2A}$ and $D_2$ receptor knockout mice. Chen et al. (2001b).

Physiological and pathophysiological functions of $A_{2A}$ receptors in L-DOPA motor complications in Parkinson's disease are far from clear. Neuronal mechanisms of L-DOPA induced dyskinesia are generally thought to involve the indirect rather than the direct pathway. Crossman (1990). L-DOPA-induced dyskinesias arise when the activity in the STN or GPi falls below a given level as a consequence of excessive inhibition from the GPe. Obeso et al. (1997). Another hypothesis that abnormalities primarily in the direct pathway might contribute significantly to the genesis of L-DOPA-induced dyskinesia isproposed.

The neuroprotective effect of $A_{2A}$ receptor antagonists has been demonstrated in neurotoxin (MPTP or 6-hydroxydopamine)-induced dopaminergic neurodegeneration in rats and mice and $A_{2A}$ receptor knock-out mice. Ikeda et al. (2002); and Chen et al. (2001a). To date, no treatment has been successful in interfering with the basic pathogenic mechanism, which results in the death of dopaminergic neurons.

Therefore, non-dopaminergic drug therapies, which effect an adenosine $A_{2A}$ receptor blockade, offer a means to treat Parkinson's disease. Moreover, adenosine $A_{2A}$ receptor antagonists, which provide antiparkinsonian effects with little or no risk of typical dopaminergic drug adverse effects, i.e., increasing or developing motor complications, are desirable.

Some xanthine compounds are known to show adenosine $A_{2A}$ receptor antagonistic activity, anti-Parkinson's disease activity, antidepressant activity, inhibitory activity on neurodegeneration, or the like (U.S. Pat. Nos. 5,484,920; 5,587,378; and 5,543,415; EP 1016407A1; etc.)

SUMMARY OF THE INVENTION

The present invention provides methods of reducing or suppressing the adverse effectiveness of L-DOPA therapy comprising administration or co-administration of one or more $A_{2A}$ receptor antagonists to Parkinson's disease patients. Such treatment can be therapeutic such as to treat patients suffering from L-DOPA- or other dopaminergic-agent-induced motor complications to reduce OFF time and/or to improve dyskinesias.

The present invention further provides methods and compositions for L-DOPA-sparing treatment. The method comprises administering to a patient in need thereof a combination of a sub-clinically effective amount of L-DOPA and one or more adenosine $A_{2A}$ receptor antagonists in an amount effective to render the L-DOPA efficacious.

The present invention further provides methods of treating Parkinson's disease and/or L-DOPA motor complications, comprising administering an effective amount of at least one adenosine $A_{2A}$ receptor antagonist in combination with a COMT inhibitor and/or DA and/or MAO inhibitor.

The present invention also provides methods of prolonging effective treatment of Parkinson's disease comprising administering to a patient in need thereof either an adenosine $A_{2A}$ receptor antagonist or a combination of an adenosine $A_{2A}$ receptor antagonist and a dopamine agonist without prior or subsequent administration of L-DOPA or dopaminergic agents, such that the patient's need for add-on L-DOPA therapy is delayed or removed entirely, delaying the onset of or preventing the development of L-DOPA motor complications.

The invention also includes methods of treating movement disorders comprising administering an effective amount of at least one adenosine $A_{2A}$ receptor antagonist to a patient in need thereof. Such treatment can be therapeutic such as to treat tremors, bradykinesias, gait, dystonias, dyskinesias, tardive dyskinesias, or other extrapyramidal syndromes, or preventative such as to prevent or lessen the effects of drugs that cause movement disorders.

BRIEF DESCRIPTION OF THE DRAWINGS

FIG. 5 is a graph depicting the time courses of the effect of KW-6002 and L-DOPA on nigral GABA (5A) and glutamate (5B) levels in chronically L-DOPA-treated 6-hydroxydopamine lesion rats. L-DOPA increased glutamate levels without effect on nigral GABA levels. KW-6002 gave no or little effects on nigral GABA and glutamate levels.

Figure 1:
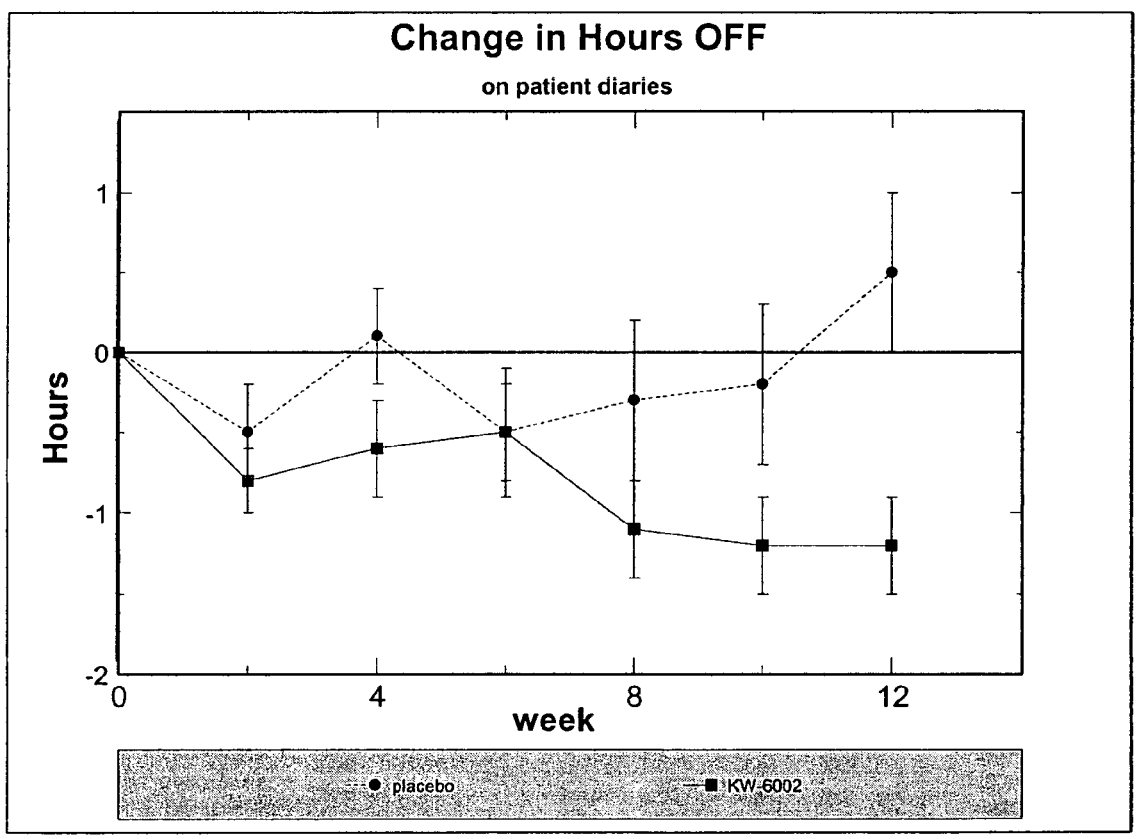
FIG. 1 is a graph depicting the change in hours OFF as recorded on home diaries for placebo and combined KW-6002 groups. At 12 weeks, subjects treated with KW-6002 had a significantly greater reduction in hours OFF (*p=0.004).

KW-6002 showed significant reduction of L-DOPA induced dyskinesias by chronic treatment for 21 days.

DETAILED DESCRIPTION OF THE INVENTION

The present invention relates to the following (1) to (50).

(1) A method of reducing or suppressing the adverse effectiveness of L-DOPA and/or dopamine agonist therapy, comprising administering an effective amount of at least one adenosine $A_{2A}$ receptor antagonist to a Parkinson's disease patient.

(2) The method according to the above (1) wherein the patient suffers from L-DOPA- or other dopaminergic-agent-induced motor complications.

(3) The method according to the above (2) wherein OFF time in motor fluctuations is reduced.

(4) The method according to the above (2) wherein dyskinesias in motor complications are improved.

(5) The method according to the above (1) wherein the adenosine $A_{2A}$ receptor antagonist is a xanthine derivative or a pharmaceutically acceptable salt thereof.

(6) The method according to the above (1) wherein the adenosine $A_{2A}$ receptor antagonist is represented by formula (I):

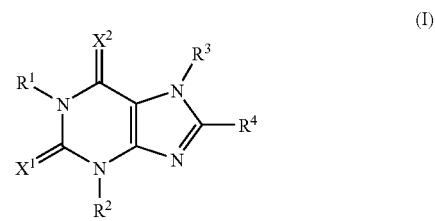

wherein
$R^1$, $R^2$ and $R^3$ represent independently hydrogen, lower alkyl, lower alkenyl or lower alkynyl; $R^4$ represents cycloalkyl, —$(CH_2)_n$—$R^5$ (in which $R^5$ represents substituted or unsubstituted aryl, or a substituted or unsubstituted heterocyclic group; and n is an integer of 0 to 4), or

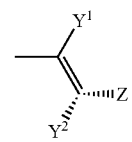

{in which $Y^1$ and $Y^2$ represent independently hydrogen, halogen, or lower alkyl; and Z represents substituted or unsubstituted aryl, or

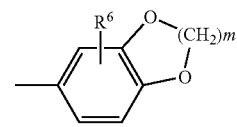

(in which $R^6$ represents hydrogen, hydroxy, lower alkyl, lower alkoxy, halogen, nitro, or amino; and m represents an integer of 1 to 3)}; and $X^1$ and $X^2$ represent independently O or S.

(7) The method according to the above (1) wherein the adenosine $A_{2A}$ receptor antagonist is represented by formula (I-A):

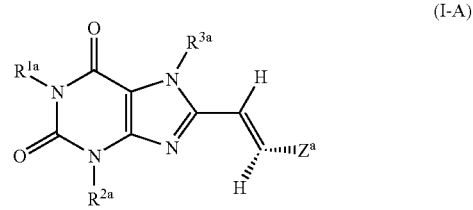

wherein $R^{1a}$ and $R^{2a}$ represent independently methyl or ethyl; $R^{3a}$ represents hydrogen or lower alkyl; and $Z^a$ represents

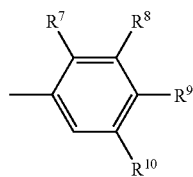

(in which at least one of $R^7$, $R^8$ and $R^9$ represents lower alkyl or lower alkoxy and the others represent hydrogen; $R^{10}$ represents hydrogen or lower alkyl) or

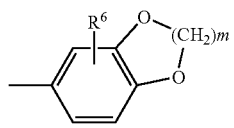

(in which $R^6$ and m have the same meanings as defined above, respectively).

(8) The method according to the above (1) wherein the adenosine $A_{2A}$ receptor antagonist is represented by formula (I-B):

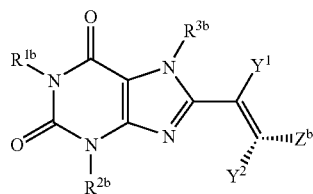

(I-B)

wherein $R^{1b}$ and $R^{2b}$ represent independently hydrogen, propyl, butyl, lower alkenyl or lower alkynyl; $R^{3b}$ represents hydrogen or lower alkyl; $Z^b$ represents substituted or unsubstituted naphthyl, or

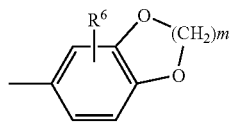

(in which $R^6$ and m have the same meanings as defined above); and $Y^1$ and $Y^2$ have the same meanings as defined above, respectively.

(9) The method according to the above (1) wherein the adenosine $A_{2A}$ receptor antagonist is (E)-8-(3,4-dimethoxystyryl)-1,3-diethyl-7-methylxanthine.

(10) A method for L-DOPA sparing treatment comprising administering to a patient in need thereof a combination of a sub-clinically effective amount of L-DOPA and one or more adenosine $A_{2A}$ receptor antagonists in an amount effective to render the L-DOPA efficacious.

(11) The method according to the above (10) wherein the adenosine $A_{2A}$ receptor antagonist is a xanthine derivative or a pharmaceutically acceptable salt thereof.

(12) The method according to the above (10) wherein the adenosine $A_{2A}$ receptor antagonist is represented by formula (I):

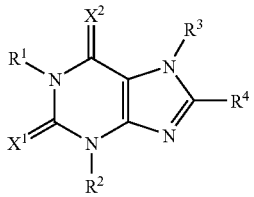

(I)

wherein
$R^1$, $R^2$ and $R^3$ represent independently hydrogen, lower alkyl, lower alkenyl or lower alkynyl; $R^4$ represents cycloalkyl, $-(CH_2)_n-R^5$ (in which $R^5$ represents substituted or unsubstituted aryl, or a substituted or unsubstituted heterocyclic group; and n is an integer of 0 to 4), or

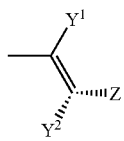

{in which $Y^1$ and $Y^2$ represent independently hydrogen, halogen, or lower alkyl; and Z represents substituted or unsubstituted aryl, or

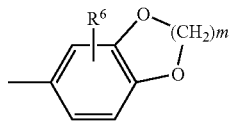

(in which $R^6$ represents hydrogen, hydroxy, lower alkyl, lower alkoxy, halogen, nitro, or amino; and m represents an integer of 1 to 3)}; and $X^1$ and $X^2$ represent independently O or S.

(13) The method according to the above (10) wherein the adenosine $A_{2A}$ receptor antagonist is represented by formula (I-A):

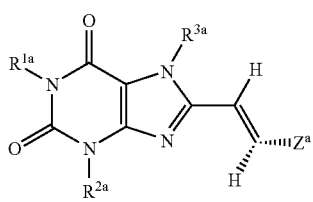

(I-A)

wherein $R^{1a}$ and $R^{2a}$ represent independently methyl or ethyl; $R^{3a}$ represents hydrogen or lower alkyl; and $Z^a$ represents

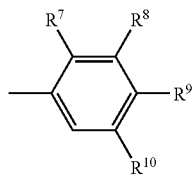

(in which at least one of $R^7$, $R^8$ and $R^9$ represents lower alkyl or lower alkoxy and the others represent hydrogen; $R^{10}$ represents hydrogen or lower alkyl) or

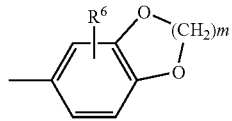

(in which $R^6$ and m have the same meanings as defined above, respectively).

(14) The method according to the above (10) wherein the adenosine $A_{2A}$ receptor antagonist is represented by formula (I-B):

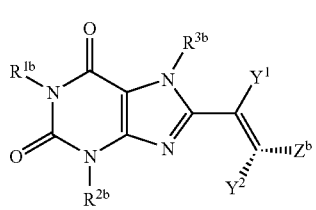

(I-B)

wherein $R^{1b}$ and $R^{2b}$ represent independently hydrogen, propyl, butyl, lower alkenyl or lower alkynyl; $R^{3b}$ represents hydrogen or lower alkyl; $Z^b$ represents substituted or unsubstituted naphthyl, or

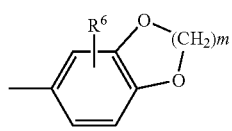

(in which $R^6$ and m have the same meanings as defined above, respectively); and $Y^1$ and $Y^2$ have the same meanings as defined above, respectively.

(15) The method according to the above (10) wherein the adenosine $A_{2A}$ receptor antagonist is (E)-8-(3,4-dimethoxystyryl)-1,3-diethyl-7-methylxanthine.

(16) A composition for L-DOPA sparing treatment comprising a sub-clinically effective amount of L-DOPA and one or more adenosine $A_{2A}$ receptor antagonists in an amount of effective to render the L-DOPA efficacious.

(17) The composition according to the above (16) wherein the adenosine $A_{2A}$ receptor antagonist is a xanthine derivative or a pharmaceutically acceptable salt thereof.

(18) The composition according to the above (16) wherein the adenosine $A_{2A}$ receptor antagonist is represented by formula (I):

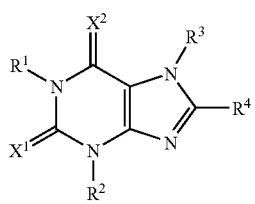

(I)

wherein
$R^1$, $R^2$ and $R^3$ represent independently hydrogen, lower alkyl, lower alkenyl or lower alkynyl; $R^4$ represents cycloalkyl, —(CH$_2$)$_n$—$R^5$ (in which $R^5$ represents substituted or unsubstituted aryl, or a substituted or unsubstituted heterocyclic group; and n is an integer of 0 to 4), or

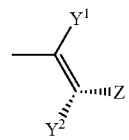

{in which $Y^1$ and $Y^2$ represent independently hydrogen, halogen, or lower alkyl; and Z represents substituted or unsubstituted aryl, or

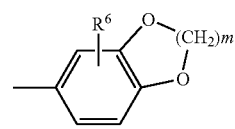

(in which $R^6$ represents hydrogen, hydroxy, lower alkyl, lower alkoxy, halogen, nitro, or amino; and m represents an integer of 1 to 3)}; and $X^1$ and $X^2$ represent independently O or S.

(19) The composition according to the above (16) wherein the adenosine $A_{2A}$ receptor antagonist is represented by formula (I-A):

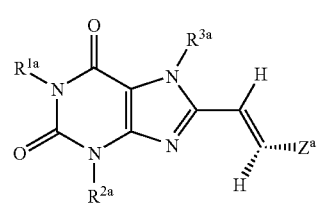

(I-A)

wherein $R^{1a}$ and $R^{2a}$ represent independently methyl or ethyl; $R^{3a}$ represents hydrogen or lower alkyl; and $Z^a$ represents

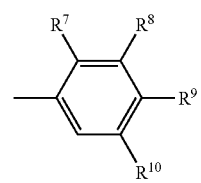

(in which at least one of $R^7$, $R^8$ and $R^9$ represents lower alkyl or lower alkoxy and the others represent hydrogen; $R^{10}$ represents hydrogen or lower alkyl) or

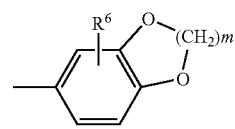

(in which $R^6$ and m have the same meanings as defined above, respectively).

(20) The composition according to the above (16) wherein the adenosine $A_{2A}$ receptor antagonist is represented by formula (I-B):

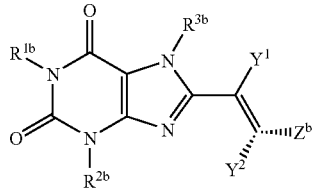

(I-B)

wherein $R^{1b}$ and $R^{2b}$ represent independently hydrogen, propyl, butyl, lower alkenyl or lower alkynyl; $R^{3b}$ represents hydrogen or lower alkyl; $Z^b$ represents substituted or unsubstituted naphthyl, or

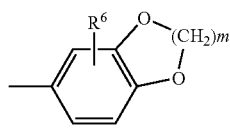

(in which $R^6$ and m have the same meanings as defined above, respectively); and $Y^1$ and $Y^2$ have the same meanings as defined above, respectively.

(21) The composition according to the above (16) wherein the adenosine $A_{2A}$ receptor antagonist is (E)-8-(3,4-dimethoxystyryl)-1,3-diethyl-7-methylxanthine.

(22) A method of treating Parkinson's disease and/or L-DOPA motor complications, comprising administering an effective amount of at least one adenosine $A_{2A}$ receptor antagonist in combination with a COMT inhibitor and/or DA and/or MAO inhibitor to a patient in need thereof.

(23) The method according to the above (22) wherein the adenosine $A_{2A}$ receptor antagonist is a xanthine derivative or a pharmaceutically acceptable salt thereof.

(24) The method according to the above (22) wherein the adenosine $A_{2A}$ receptor antagonist is represented by formula (I):

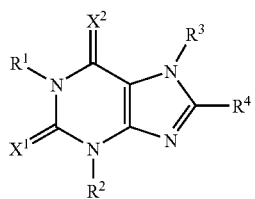

(I)

wherein $R^1$, $R^2$ and $R^3$ represent independently hydrogen, lower alkyl, lower alkenyl or lower alkynyl; $R^4$ represents cycloalkyl, $-(CH_2)_n-R^5$ (in which $R^5$ represents substituted or unsubstituted aryl, or a substituted or unsubstituted heterocyclic group; and n is an integer of 0 to 4), or

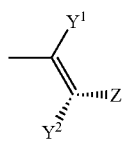

{in which $Y^1$ and $Y^2$ represent independently hydrogen, halogen, or lower alkyl; and Z represents substituted or unsubstituted aryl, or

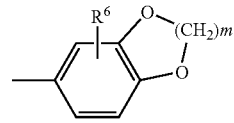

(in which $R^6$ represents hydrogen, hydroxy, lower alkoxy, lower alkoxy, halogen, nitro, or amino; and m represents an integer of 1 to 3)}; and $X^1$ and $X^2$ represent independently O or S.

(25) The method according to the above (22) wherein the adenosine $A_{2A}$ receptor antagonist is represented by formula (I-A):

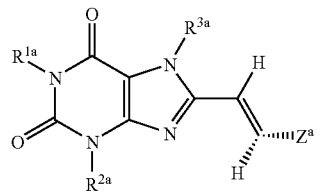

(I-A)

wherein $R^{1a}$ and $R^{2a}$ represent independently methyl or ethyl; $R^{3a}$ represents hydrogen or lower alkyl; and $Z^a$ represents

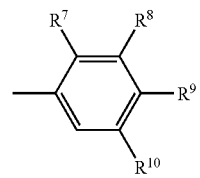

(in which at least one of $R^7$, $R^8$ and $R^9$ represents lower alkyl or lower alkoxy and the others represent hydrogen; $R^{10}$ represents hydrogen or lower alkyl) or

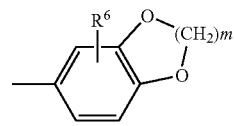

(in which $R^6$ and m have the same meanings as defined above, respectively).

(26) The method according to the above (22) wherein the adenosine $A_{2A}$ receptor antagonist is represented by formula (I-B):

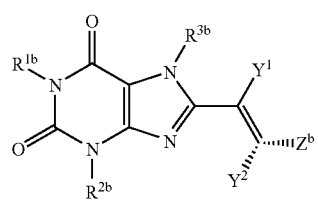

(I-B)

wherein $R^{1b}$ and $R^{2b}$ represent independently hydrogen, propyl, butyl, lower alkenyl or lower alkynyl; $R^{3b}$ represents hydrogen or lower alkyl; $Z^b$ represents substituted or unsubstituted naphthyl, or

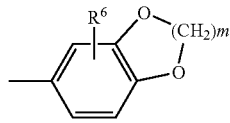

(in which $R^6$ and m have the same meanings as defined above, respectively); and $Y^1$ and $Y^2$ have the same meanings as defined above, respectively.

(27) The method according to the above (22) wherein the adenosine $A_{2A}$ receptor antagonist is (E)-8-(3,4-dimethoxystyryl)-1,3-diethyl-7-methylxanthine.

(28) A composition for the treatment of Parkinson's disease comprising an effective amount of at least one adenosine $A_{2A}$ receptor antagonist, and a COMT inhibitor and/or DA and/or MAO inhibitor.

(29) The composition according to the above (28) wherein the adenosine $A_{2A}$ receptor antagonist is a xanthine derivative or a pharmaceutically acceptable salt thereof.

(30) The composition according to the above (28) wherein the adenosine $A_{2A}$ receptor antagonist is represented by formula (I):

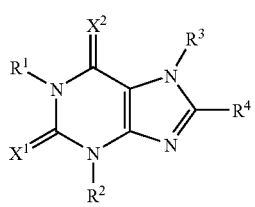

wherein $R^1$, $R^2$ and $R^3$ represent independently hydrogen, lower alkyl, lower alkenyl or lower alkynyl; $R^4$ represents cycloalkyl, $-(CH_2)_n-R^5$ (in which $R^5$ represents substituted or unsubstituted aryl, or a substituted or unsubstituted heterocyclic group; and n is an integer of 0 to 4), or

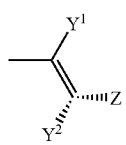

{in which $Y^1$ and $Y^2$ represent independently hydrogen, halogen, or lower alkyl; and Z represents substituted or unsubstituted aryl, or

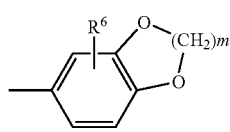

(in which $R^6$ represents hydrogen, hydroxy, lower alkyl, lower alkoxy, halogen, nitro, or amino; and m represents an integer of 1 to 3)}; and $X^1$ and $X^2$ represent independently O or S.

(31) The composition according to the above (28) wherein the adenosine $A_{2A}$ receptor antagonist is represented by formula (I-A):

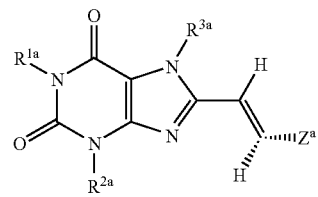

wherein $R^{1a}$ and $R^{2a}$ represent independently methyl or ethyl; $R^{3a}$ represents hydrogen or lower alkyl; and $Z^a$ represents

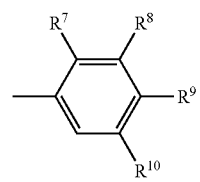

(in which at least one of $R^7$, $R^8$ and $R^9$ represents lower alkyl or lower alkoxy and the others represent hydrogen; $R^{10}$ represents hydrogen or lower alkyl) or

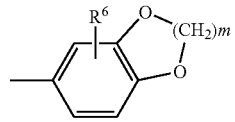

(in which $R^6$ and m have the same meanings as defined above, respectively).

(32) The composition according to the above (28) wherein the adenosine $A_{2A}$ receptor antagonist is represented by formula (I-B):

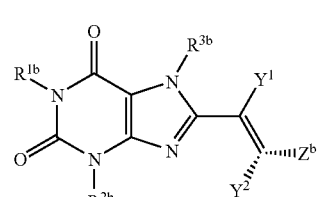

wherein $R^{1b}$ and $R^{2b}$ represent independently hydrogen, propyl, butyl, lower alkenyl or lower alkynyl; $R^{3b}$ represents hydrogen or lower alkyl; $Z^b$ represents substituted or unsubstituted naphthyl, or

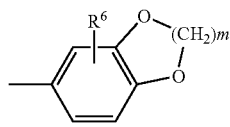

(in which $R^6$ and m have the same meanings as defined above, respectively); and $Y^1$ and $Y^2$ have the same meanings as defined above, respectively.

(33) The composition according to the above (28) wherein the adenosine $A_{2A}$ receptor antagonist is (E)-8-(3,4-dimethoxystyryl)-1,3-diethyl-7-methylxanthine.

(34) A method of prolonging effective treatment of Parkinson's disease comprising administering to a patient in need thereof either an adenosine $A_{2A}$ receptor antagonist or a combination of an adenosine $A_{2A}$ receptor antagonist and a dopamine agonist in an amount effective to delay or remove the patient's need for add-on L-DOPA therapy.

(35) The method according to the above (34) wherein the development of motor complications is delayed.

(36) The method according to the above (34) wherein the patient has not had prior administration of L-DOPA or a dopaminergic agent.

(37) The method according to the above (34) wherein the patient does not have subsequent administration of L-DOPA or a dopaminergic agent.

(38) The method according to the above (34) wherein the adenosine $A_{2A}$ receptor antagonist is a xanthine derivative or a pharmaceutically acceptable salt thereof.

(39) The method according to the above (34) wherein the adenosine $A_{2A}$ receptor antagonist is represented by formula (I):

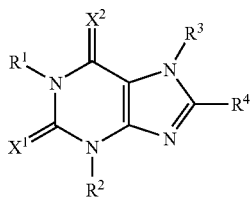

(I)

wherein $R^1$, $R^2$ and $R^3$ represent independently hydrogen, lower alkyl, lower alkenyl or lower alkynyl; $R^4$ represents cycloalkyl, —$(CH_2)_n$—$R^5$ (in which $R^5$ represents substituted or unsubstituted aryl, or a substituted or unsubstituted heterocyclic group; and n is an integer of 0 to 4), or

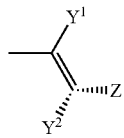

{in which $Y^1$ and $Y^2$ represent independently hydrogen, halogen, or lower alkyl; and Z represents substituted or unsubstituted aryl, or

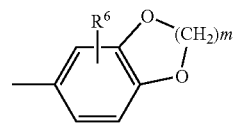

(in which $R^6$ represents hydrogen, hydroxy, lower alkyl, lower alkoxy, halogen, nitro, or amino; and m represents an integer of 1 to 3)}; and $X^1$ and $X^2$ represent independently O or S.

(40) The method according to the above (34) wherein the adenosine $A_{2A}$ receptor antagonist is represented by formula (I-A):

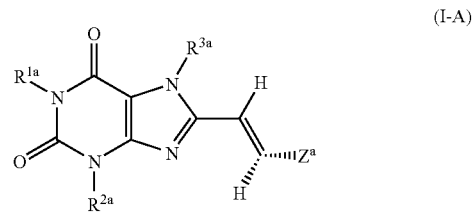

(I-A)

wherein $R^{1a}$ and $R^{2a}$ represent independently methyl or ethyl; $R^{3a}$ represents hydrogen or lower alkyl; and $Z^a$ represents

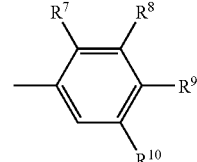

(in which at least one of $R^7$, $R^8$ and $R^9$ represents lower alkyl or lower alkoxy and the others represent hydrogen; $R^{10}$ represents hydrogen or lower alkyl) or

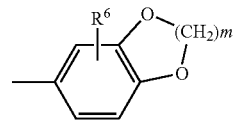

(in which $R^6$ and m have the same meanings as defined above, respectively).

(41) The method according to the above (34) wherein the adenosine $A_{2A}$ receptor antagonist is represented by formula (I-B):

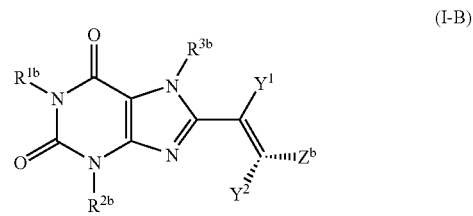

(I-B)

wherein R$^{1b}$ and R$^{2b}$ represent independently hydrogen, propyl, butyl, lower alkenyl or lower alkynyl; R$^{3b}$ represents hydrogen or lower alkyl; Z$^b$ represents substituted or unsubstituted naphthyl, or

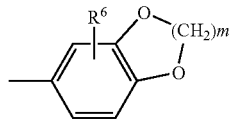

(in which R$^6$ and m have the same meanings as defined above, respectively); and Y$^1$ and Y$^2$ have the same meanings as defined above, respectively.

(42) The method according to the above (34) wherein the adenosine A$_{2A}$ receptor antagonist is (E)-8-(3,4-dimethoxystyryl)-1,3-diethyl-7-methylxanthine.

(43) A method of treating movement disorders comprising administrating an effective amount of at least one adenosine A$_{2A}$ receptor antagonist to a patient in need thereof.

(44) The method according to the above (43) wherein the patient suffers from tremors, bradykinesias, gait, dystonias, dyskinesias, tardive dyskinesias or other extrapyramidal syndromes.

(45) The method according to the above (43) wherein the adenosine A$_{2A}$ receptor antagonist lessens the effects of drugs that cause movement disorders.

(46) The method according to the above (43) wherein the adenosine A$_{2A}$ receptor antagonist is a xanthine derivative or a pharmaceutically acceptable salt thereof.

(47) The method according to the above (43) wherein the adenosine A$_{2A}$ receptor antagonist is represented by formula (I):

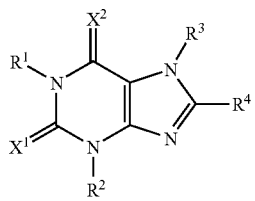

(I)

wherein

R$^1$, R$^2$ and R$^3$ represent independently hydrogen, lower alkyl, lower alkenyl or lower alkynyl; R$^4$ represents cycloalkyl, —(CH$_2$)$_n$—R$^5$ (in which R$^5$ represents substituted or unsubstituted aryl, or a substituted or unsubstituted heterocyclic group; and n is an integer of 0 to 4), or

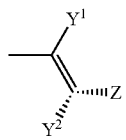

{in which Y$^1$ and Y$^2$ represent independently hydrogen, halogen, or lower alkyl; and Z represents substituted or unsubstituted aryl, or

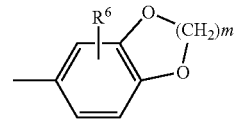

(in which R$^6$ represents hydrogen, hydroxy, lower alkyl, lower alkoxy, halogen, nitro, or amino; and m represents an integer of 1 to 3)}; and X$^1$ and X$^2$ represent independently O or S.

(48) The method according to the above (43) wherein the adenosine A$_{2A}$ receptor antagonist is represented by formula (I-A)

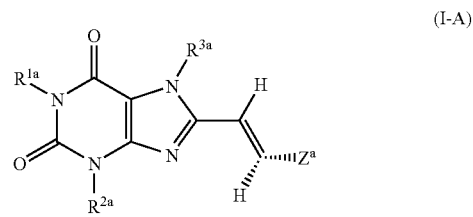

(I-A)

wherein R$^{1a}$ and R$^{2a}$ represent independently methyl or ethyl; R$^{3a}$ represents hydrogen or lower alkyl; and Z$^a$ represents

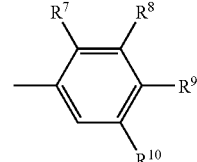

(in which at least one of R$^7$, R$^8$ and R$^9$ represents lower alkyl or lower alkoxy and the others represent hydrogen; R$^{10}$ represents hydrogen or lower alkyl) or

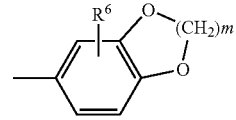

(in which R$^6$ and m have the same meanings as defined above, respectively).

(49) The method according to the above (43) wherein the adenosine A$_{2A}$ receptor antagonist is represented by formula (I-B):

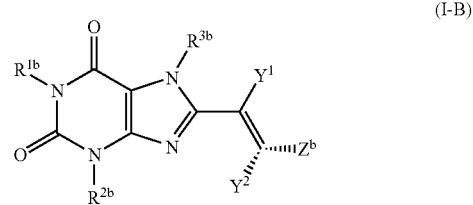

(I-B)

wherein $R^{1b}$ and $R^{2b}$ represent independently hydrogen, propyl, butyl, lower alkenyl or lower alkynyl; $R^{3b}$ represents hydrogen or lower alkyl; $Z^b$ represents substituted or unsubstituted naphthyl, or

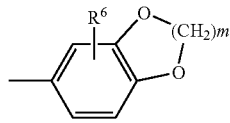

(in which $R^6$ and m have the same meanings as defined above, respectively); and $Y^1$ and $Y^2$ have the same meanings as defined above, respectively.

(50) The method according to the above (43) wherein the adenosine $A_{2A}$ receptor antagonist is (E)-8-(3,4-dimethoxystyryl)-1,3-diethyl-7-methylxanthine.

The present invention is directed to methods of treating patients suffering from movement disorders comprising administering one or more adenosine $A_{2A}$ receptor antagonists. By "adenosine $A_{2A}$ receptor antagonist" is meant a compound that inhibits, suppresses or causes the cessation of at least one adenosine-mediated biological activity by, e.g., binding to adenosine $A_{2A}$ receptors, interfering with, or preventing the binding of adenosine to the receptor.

The present invention contemplates that adenosine $A_{2A}$ receptor antagonists can be used to treat movement disorders, since the adenosine $A_{2A}$ receptor functions, for example, in controlling the indirect pathway or basal ganglia output nuclei activity. The adenosine $A_{2A}$ receptors are also considered to be involved in controlling motor behavior or motor dysfunctions.

An adenosine $A_{2A}$ receptor antagonist functions in several ways. The antagonist may bind to or sequester adenosine with sufficient affinity and specificity to substantially interfere with, block or otherwise prevent binding of adenosine to an adenosine $A_{2A}$ receptor, thereby inhibiting, suppressing or causing the cessation of one or more adenosine $A_{2A}$ receptor-mediated biological functions, such as modulation of striatal GABAergic output of the indirect pathway, and activities of the basal ganglia output nuclei, SNr, for example, thereby controlling motor behaviors in basal ganglia. The present invention contemplates that antiparkinsonian activity of the adenosine $A_{2A}$ receptor antagonist results from this activity. The present invention further contemplates that the capability of the adenosine $A_{2A}$ receptor antagonist to reduce or suppress the adverse effectiveness of L-DOPA and/or dopamine agonist therapy in Parkinson's disease patients results from this activity. The present invention further contemplate that involvement of the adenosine receptor antagonists in development of L-DOPA and/or dopamine agonist induced motor complications results from this activity. Alternatively, an adenosine $A_{2A}$ receptor antagonist may inhibit neuron degeneration cascades induced by dopaminergic neurotoxins such as 6-OHDA (6-hydroxydopamine) and 1-methyl-4-phenyl-1,2,3,6-tetrahydropyridine (MPTP) and dopaminergic neurotoxin production via glial cells. Accordingly, adenosine $A_{2A}$ receptor antagonists provide methods of inhibiting the dopaminergic neurodegenerative effects of neurotoxins and also inhibiting gliosis. These features of adenosine $A_{2A}$ receptor antagonists prevent the progress of Parkinson's disease. Thus, the use of adenosine $A_{2A}$ receptor antagonists provide therapy such that the patient's need for add-on L-DOPA therapy is delayed or removed entirely, or delaying the onset of or preventing the development of L-DOPA motor complications.

The adenosine $A_{2A}$ receptor antagonists of the present invention are thus directed to methods of treating Parkinson's disease patients and other patients suffering from movement disorders by administering an effective amount of one or more adenosine $A_{2A}$ receptor antagonists. The adenosine $A_{2A}$ receptor antagonists of the present invention are also useful in methods of reducing or suppressing the adverse effectiveness of L-DOPA therapy including L-DOPA motor complications in the treatment of Parkinson's disease. Furthermore, treatment of Parkinson's disease with adenosine $A_{2A}$ receptor antagonists can avoid the need for treatment with L-DOPA and reduce the amounts of L-DOPA required to effectively treat Parkinson's disease in the absence or reduction of side effects such as, nausea, hyperactivity, motor fluctuations such as wearing off and ON-OFF fluctuations, and dyskinesia. The present invention further provides methods for treating Parkinson's disease patients by administering adenosine $A_{2A}$ receptor antagonists such that the patient's need for L-DOPA therapy is delayed or removed entirely, delaying the onset of or preventing the development of L-DOPA motor complications. The present invention further provides methods for treating tremors, bradykinesias, gait, dystonias, and tardive dyskinesias and other extrapyramidal syndromes in patients suffering from other movement disorders.

The adenosine $A_{2A}$ receptor antagonist used in the present invention is not limited as long as it has $A_{2A}$ receptor antagonistic activity. Examples thereof include compounds disclosed in U.S. Pat. No. 5,484,920, U.S. Pat. No. 5,703,085, WO 92/06976, WO 94/01114, U.S. Pat. No. 5,565,460, WO 98/42711, WO 00/17201, WO 99/43678, WO 01/92264, WO 99/35147, WO 00/13682, WO 00/13681, WO 00/69464, WO 01/40230, WO 01/02409, WO 01/02400, EP 1054012, WO 01/62233, WO 01/17999, WO 01/80893, WO 02/14282, WO 01/97786, and the like. More specifically, examples include:

(1) compounds represented by the following formula (I):

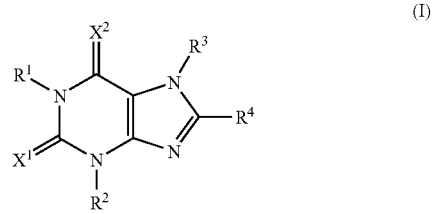

wherein $R^1$, $R^2$ and $R^3$ represent independently hydrogen, lower alkyl, lower alkenyl or lower alkynyl; $R^4$ represents cycloalkyl, —(CH$_2$)$_n$—$R^5$ (in which $R^5$ represents substituted or unsubstituted aryl, or a substituted or unsubstituted heterocyclic group; and n is an integer of 0 to 4), or

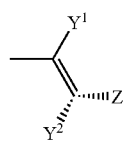

{in which $Y^1$ and $Y^2$ represent independently hydrogen, halogen, or lower alkyl; and Z represents substituted or unsubstituted aryl, or

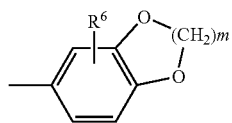

(in which $R^6$ represents hydrogen, hydroxy, lower alkyl, lower alkoxy, halogen, nitro, or amino; and m represents an integer of 1 to 3)}; and $X^1$ and $X^2$ represent independently O or S, (2) compounds represented by the following formula (I-A):

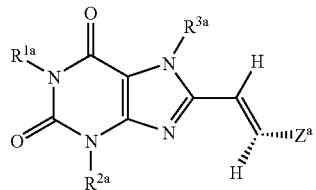

(I-A)

wherein $R^{1a}$ and $R^{2a}$ represent independently methyl or ethyl; $R^{3a}$ represents hydrogen or lower alkyl; and $Z^a$ represents

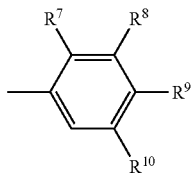

(in which at least one of $R^7$, $R^8$ and $R^9$ represents lower alkyl or lower alkoxy and the others represent hydrogen; $R^{10}$ represents hydrogen or lower alkyl) or

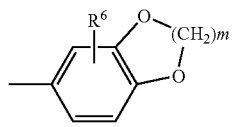

(in which $R^6$ and m have the same meanings as defined above, respectively), and (3) compounds represented by the following formula (I-B):

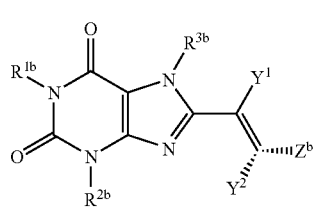

(I-B)

wherein $R^{1b}$ and $R^{2b}$ represent independently hydrogen, propyl, butyl, lower alkenyl or lower alkynyl; $R^{3b}$ represents hydrogen or lower alkyl; $Z^b$ represents substituted or unsubstituted naphthyl, or

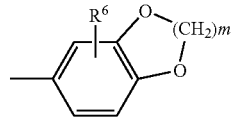

(in which $R^6$ and m have the same meanings as defined above, respectively); and $Y^1$ and $Y^2$ have the same meanings as defined above, respectively, and pharmaceutically acceptable salts thereof.

In the definitions of the groups of formula (I), formula (I-A), and formula (I-B), the lower alkyl and the lower alkyl moiety of the lower alkoxy mean a straight-chain or branched alkyl group having 1 to 6 carbon atoms, such as methyl, ethyl, propyl, isopropyl, butyl, isobutyl, sec-butyl, tert-butyl, pentyl, neopentyl, and hexyl. The lower alkenyl means a straight-chain or branched alkenyl group having 2 to 6 carbon atoms, such as vinyl, allyl, methacryl, crotyl, 3-butenyl, 2-pentenyl, 4-pentenyl, 2-hexenyl, and 5-hexenyl. The lower alkynyl means a straight-chain or branched alkynyl group having 2 to 6 carbon atoms, such as ethynyl, propargyl, 2-butynyl, 3-butynyl, 2-pentynyl, 4-pentynyl, 2-hexynyl, 5-hexynyl, and 4-methyl-2-pentynyl. The aryl means phenyl or naphthyl. The cycloalkyl means a cycloalkyl group having 3 to 8 carbon atoms, such as cyclopropyl, cyclobutyl, cyclopentyl, cyclohexyl, cycloheptyl, and cyclooctyl. Examples of the heterocyclic group are furyl, thienyl, pyrrolyl, pyranyl, thiopyranyl, pyridyl, thiazolyl, imidazolyl, pyrimidyl, triazinyl, indolyl, quinolyl, purinyl, and benzothiazolyl. The halogen includes fluorine, chlorine, bromine, and iodine.

The substituted aryl, the substituted heterocyclic group, and the substituted naphthyl each have 1 to 4 independently selected substituents. Examples of the substituents are lower alkyl, hydroxy, substituted or unsubstituted lower alkoxy, halogen, nitro, amino, lower alkylamino, di(lower alkyl) amino, trifluoromethyl, trifluoromethoxy, benzyloxy, phenyl, and phenoxy. The lower alkyl and the lower alkyl moiety of the lower alkoxy, lower alkylamino, and di(lower alkyl) amino have the same meaning as the lower alkyl defined above. The halogen has the same meaning as the halogen defined above. Examples of the substituent of the substituted lower alkoxy are hydroxy, lower alkoxy, halogen, amino, azide, carboxy, and lower alkoxycarbonyl. The lower alkyl moiety of the lower alkoxy and lower alkoxycarbonyl has the same meaning as the lower alkyl defined above, and the halogen has the same meaning as the halogen defined above.

The above-mentioned pharmaceutically acceptable salts of Compounds (I), Compounds (I-A), and Compounds (I-B) include pharmaceutically acceptable acid addition salts, metal salts, ammonium salts, organic amine addition salts, and amino acid addition salts.

Examples of the pharmaceutically acceptable acid addition salts are inorganic acid addition salts such as hydrochloride, sulfate and phosphate, and organic acid addition salts such as acetate, maleate, fumarate, tartrate, and citrate. Examples of the pharmaceutically acceptable metal salts are alkali metal salts such as sodium salt and potassium salt, alkaline earth metal salts such as magnesium salt and calcium salt, aluminum salt and zinc salt. Examples of the pharmaceutically acceptable ammonium salts are ammonium and tetramethylammonium. Examples of the pharmaceutically acceptable organic amine addition salts are salts with morpholine and piperidine. Examples of the pharmaceutically acceptable amino acid addition salts are salts with lysine, glycine and phenylalanine.

Compounds represented by formula (I), formula (I-A), and formula (I-B) are described and synthesized in accordance with the methodology described in U.S. Pat. Nos. 5,543,415; 5,587,378; and 5,484,920.

A preferred adenosine $A_{2A}$ receptor antagonist useful in accordance with the methods of the present invention comprises (E)-8-(3,4-dimethoxystyryl)-1,3-diethyl-7-methylxanthine (the following formula (II)).

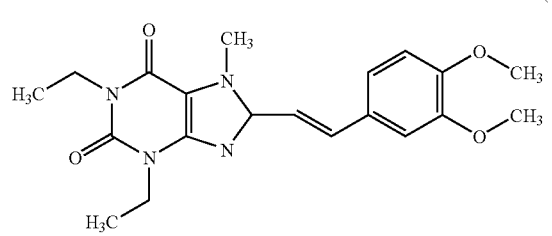

(II)

Formula II is also identified in accordance with the present invention as KW-6002.

By "reducing or suppressing the adverse effectiveness of L-DOPA" is understood in accordance with the present invention to mean that the compounds of the present invention reduce the patients' amount of awake time in an "OFF" state. An OFF state is understood in accordance with the invention to mean the period of time where the therapeutic benefit of a dose of a parkinsonian medication have worn off, such that the patient experiences symptoms of Parkinson's disease such as are classified by the Unified Parkinson's Disease Rating Scale (UPDRS) and the Hoehn and Yahr (HY) scale, for example.

The present invention is also directed to reducing the adverse effectiveness of L-DOPA by increasing the proportion of the patients' awake time in an "ON" state. By ON state is meant, the period of time following a dose of a parkinsonian medication during which the patient is relatively free of the symptoms of Parkinson's Disease as classified by the UPDRS and the HY scale. Patients treatable by the methods of the present invention include patients at early, intermediate and advanced stages of Parkinson's disease with or without motor complications as determined by the Parkinson Dyskinesia Scale (PDS). Dyskinesias can be separately measured by the UPDRS, modified Goetz Dyskinesia Rating Scale (MGDRS), and/or Abnormal Involuntary Movement Scale (AIMS). The treatment contemplated by the present invention is especially effective in patients suffering from advanced Parkinson's disease.

In accordance with the present invention the adenosine $A_{2A}$ receptor antagonists of the present invention can be co-administered with L-DOPA or a dopamine agonist, i.e. administered at substantially the same time. It is also contemplated that the adenosine $A_{2A}$ receptor antagonists can be administered alone; either before or after the patient receives a dose of L-DOPA or a dopamine agonist. A substantial reduction in the requirement for L-DOPA and/or a reduction or a suppression in the typical adverse effects of L-DOPA therapy are observed with the administration of KW-6002, especially in the symptoms of motor fluctuations and dyskinesia. Thus, the present invention contemplates an improved method of treating Parkinson's disease in humans by administering KW-6002 with L-DOPA that cause motor fluctuations, dyskinesia, nausea, and other common side effects of L-DOPA therapy.

The present invention further provides a method of prolonging effective treatment of Parkinson's disease comprising the administration of either an adenosine $A_{2A}$ receptor antagonist or a combination of an adenosine $A_{2A}$ receptor antagonist and a dopamine agonist without prior or subsequent administration of L-DOPA. The requirement for L-DOPA is eliminated or at least substantially reduced together with the avoidance of the concomitant adverse side effects of L-DOPA therapy. A "combination" of an adenosine $A_{2A}$ receptor antagonist and a dopamine agonist is provided to a patient concurrently or at least in a manner such as to permit an overlap of biological activity. Since the adenosine $A_{2A}$ receptor antagonists of the invention interfere with the development of L-DOPA motor complications and also prevent dopaminergic neurodegeneration, an adenosine $A_{2A}$ receptor antagonist administered singly or together with a dopamine agonist can delay the onset of or prevent the progress of L-DOPA motor complications In accordance with the present invention, the adenosine $A_{2A}$ receptor antagonists can be administered singly or together with a dopamine agonist such as, for example, bromocriptine, cabergoline, pramipexol, ropinerole, or pergolide, and thereby avoid or at least provide an extension of time before which the need for L-DOPA manifests.

The present invention further provides methods of L-DOPA-sparing treatment of Parkinson's patients. That is, treatment with sub-clinically effective amounts of L-DOPA while maintaining the efficacy of sub-clinically effective amounts of L-DOPA. The method comprises treating the patient with sub-clinically effective amounts of L-DOPA and effective amounts of an adenosine $A_{2A}$ receptor antagonist. By sub-clinically effective amounts of L-DOPA is meant an amount of L-DOPA that is not effective in treatment of a particular patient. Typically, L-DOPA is administered at 100 mg to 1 g per day in divided doses (usually 250 mg 4 times a day). The dose is increased gradually in increments of 100 to 750 mg a day at 3- to 7-day intervals until intolerable side effects occur, usually movement disorders. When co-administered with carbidopa, effective amounts of L-DOPA are reduced. It is well within the skill of one in the art to determine the sub-clinically effective dose of L-DOPA for a particular patient and to adjust it accordingly in the presence of an adenosine $A_{2A}$ receptor antagonist.

Compositions comprising sub-clinically effective amounts of L-DOPA and optionally an adenosine $A_{2A}$ receptor antagonist and optionally a dopamine antagonist are made by methods known in the art and described herein. Additional amounts of carbidopa and other active ingredients can also be determined by one of skill in the art.

The present invention further provides methods of treating Parkinson's disease with at least one adenosine $A_{2A}$ receptor antagonist and at least one of a COMT or MAO-B inhibitor. The compositions can be administered together or sequentially, by any method known in the art. Methods of making and administering such compositions are known in the art. Suitable COMT and MAO inhibitors are described herein and are well known in the art. These include, but are not limited to, entacapone and tolcapone, and deprenyl. As shown below, concomitant treatment of adenosine $A_{2A}$ receptor antagonist and COMT or MAO-B inhibitors does not increase side effects.

By "prolonging effective treatment" is meant that the patient's Parkinson's symptoms and motor complications are reduced or inhibited either subjectively or objectively according to the UPDRS, AIMS, PDS, HY and/or MGDRS such that the patient's need for L-DOPA therapy is delayed or removed entirely.

The invention also includes methods of treating movement disorders comprising administering an effective amount of at least one adenosine $A_{2A}$ receptor antagonist to a patient in need thereof. Such treatment can be therapeutic such as to treat tremors, bradykinesias, gait, dystonias, or tardive dyskinesias or other extrapyramidal syndromes, or preventative such as to prevent or lessen the effects of drugs that cause movement disorders. Such drugs are known in the art and include, but are not limited to, those listed in Table 1.

By "treating movement disorders" is meant the cessation or diminishment of symptoms including, but not limited to, tremor, dystonia, dyskinesia, spasticity. Changes in symptoms can be measured by any method known in the art including, but not limited to, UPDRS, AIMS, PDS, HY and/or MGDRS.

The term "treatment" or "treat" refers to effective inhibition, suppression or cessation of the adenosine activity so as to improve motor dysfunction or prevent or delay the onset, retard the progression or ameliorate the symptoms of the disease or disorder.

The present invention thus provides methods of interfering with, blocking or otherwise preventing the interaction or binding of adenosine with an adenosine $A_{2A}$ receptor by employing the adenosine $A_{2A}$ receptor antagonists of the present invention.

Pharmaceutical compositions for administration according to the present invention comprise at least one adenosine $A_{2A}$ receptor antagonist optionally combined with a pharmaceutically acceptable carrier. These compositions can be administered by any means that achieve their intended purposes. Amounts and regimens for the administration of a composition according to the present invention can be readily determined by those with ordinary skill in the art in treating Parkinson's disease patients.

The compositions described herein can be administered by any suitable method including, without limitation, orally; intranasally; intrapulmonarally; parenterally, such as subcutaneously, intravenously, intramuscularly, intraperitoneally; intraduodenally; transdermally; or buccally.

The dosage administered is an effective amount and depends upon the age, health and weight of the patient, type of previous or concurrent treatment, if any, frequency of treatment, and the nature of the effect desired. Several factors are typically taken into account when determining an appropriate dosage. These factors include age, sex and weight of the patient, the condition being treated, the severity of the condition and the form of the drug being administered.

An "effective amount" is an amount sufficient to effect a beneficial or desired clinical result. An effective amount can be administered in one or more doses. In terms of treatment, an effective amount is amount that is sufficient to palliate, ameliorate, stabilize, reverse or slow the progression of the disease or disorder, or otherwise reduce the pathological consequences of the disease or disorder. The effective amount is generally determined by the physician on a case-by-case basis and is within the skill of one in the art.

In addition to pharmaceutically active compounds, compositions according to the present invention can also contain suitable pharmaceutically acceptable carriers comprising excipients that facilitate processing of the active compounds into pharmaceutically acceptable preparations. Preferably, the preparations, particularly those preparations which can be administered orally and which can be used for the preferred type of administration, such as tablets, troches and capsules, and also preparations which can be administered rectally, such as suppositories, as well as suitable solutions for administration by injection, contain from about 0.1 to 99 percent, preferably from about 20 to 85 percent of active compound(s), together with the excipient. Liquid pharmaceutically acceptable compositions can, for example, be prepared by dissolving or dispersing a compound embodied herein in a liquid excipient, such as water, saline, aqueous dextrose, glycerol, or ethanol. The composition can also contain other medicinal agents, pharmaceutical agents, carriers, and auxiliary substances such as wetting or emulsifying agents and pH buffering agents.

Pharmaceutical compositions of the present invention are administered by a mode appropriate for the form of composition. Typical routes include subcutaneous, intramuscular, intraperitoneal, intradermal, oral, intranasal, and intrapulmonary (i.e., by aerosol). Pharmaceutical compositions of this invention for human use are typically administered orally.

Pharmaceutical compositions for oral, intranasal, or topical administration can be supplied in solid, semi-solid or liquid forms, including tablets, capsules, powders, liquids, and suspensions. Compositions for injection can be supplied as liquid solutions or suspensions, as emulsions, or as solid forms suitable for dissolution or suspension in liquid prior to injection. For administration via the respiratory tract, a preferred composition is one that provides a solid, powder, or liquid aerosol when used with an appropriate aerosolizer device. Although not required, pharmaceutical compositions are preferably supplied in unit dosage form suitable for administration of a precise amount. Also contemplated by this invention are slow release or sustained release forms, whereby relatively consistent levels of the active compounds are provided over an extended period.

The adenosine $A_{2A}$ receptor antagonists may preferably be administered in an amount of from about 0.001 to about 20.0 mg per kilogram of body weight. A dosage range of from about 0.01 to about 10 mg per kilogram of body weight is more preferable. Since the adenosine $A_{2A}$ receptor antagonist compositions of this invention will eventually be cleared from the blood stream, regarding administration of the compositions is indicated and preferred.

The adenosine $A_{2A}$ receptor antagonists can be administered in a manner compatible with the dosage formulation and in such amount as will be therapeutically effective. Systemic dosages depend on the age, weight and conditions of the patient and on the administration route.

Pharmaceutical preparations useful in the methods according to the present invention are manufactured in a known manner. The preparation of pharmaceutical compositions is conducted in accordance with generally accepted procedures for the preparation of pharmaceutical preparations. See, for example, Remington's Pharmaceutical Sciences 18th Edition (1990), Martin ed., Mack Publishing Co., PA. Depending on the intended use and mode of administration, it may be desirable to process the active ingredient further in the preparation of pharmaceutical compositions. Appropriate processing may include sterilizing, mixing with appropriate non-toxic and non-interfering components, dividing into dose units and enclosing in a delivery device.

The pharmaceutical preparations for oral use can be obtained by combining the active compounds with solid excipients, optionally grinding the resulting mixture, and processing the mixture of granules, after adding suitable auxiliaries, if desired or necessary, to obtain tablets.

Suitable excipients include, but are not limited to fillers such as saccharides, for example, lactose or sucrose, mannitol or sorbitol; cellulose derivatives; zinc compounds; calcium phosphates such as tricalcium phosphate or calcium hydrogen phosphate; as well as binders such as starch paste, using, for example, maize starch, wheat starch, rice starch, potato starch; gelatin; tragacanth; and/or polyvinylpyrrolidone.

Auxiliaries include flow-regulating agents and lubricants, such as silica, talc, stearic acid or salts thereof, and/or polyethylene glycol. Tablet, caplet or capsule cores are provided with suitable coatings, which, if desired, are resistant to gastric juices. For this purpose, concentrated saccharide solutions can be used, which can optionally contain gum Arabic, talc, polyvinyl pyrrolidone, polyethylene glycol and/or titanium dioxide, lacquer solutions and suitable organic solvents or solvent mixtures. In order to produce coatings resistant to gastric juices, i.e., enteric coatings, solutions of suitable cellulose preparations such as acetylcellulose phthalate or hydroxypropylmethyl cellulose phthalate are used. Dyes or pigments can be added to the tablets or coatings, for example, for identification or in order to characterize combinations of active compound doses.

Other pharmaceutical preparations, which can be used orally, include push-fit capsules made of gelatin, as well as soft, sealed capsules made of gelatin and a plasticizer such as glycerol or sorbitol. The push-fit capsules can contain the active compounds in the form of granules, which can be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils or liquid paraffin. In addition, stabilizers may be added.

Adenosine $A_{2A}$ receptor antagonists of the present invention can also be administered in the form of an implant when compounded with a biodegradable slow-release carrier. Alternatively, the active ingredients can be formulated as a transdermal patch for continuous release of the active ingredient. Methods of making implants and patches are well known in the art. Remington's Pharmaceutical Sciences 18th Edition (1990); and Kydonieus ed. (1992) Treatise on controlled drug delivery, Marcel Dekker, NY.

The following non-limiting Examples, further illustrate the present invention. All references cited herein are hereby incorporated by reference.

EXAMPLE 1

The safety and efficacy of the adenosine $A_{2A}$ receptor antagonist KW-6002 as a treatment for Parkinson's disease complicated by L-DOPA-related motor complications was examined in a 12-week, multicenter, exploratory study. PD subjects with motor complications were randomly and blindly assigned to 1 of 3 parallel treatment arms: placebo (n=29); KW-6002 up to 20 mg/d (n=26); KW-6002 up to 40 mg/d (n=28). There were 2 primary efficacy measures: 1) change in "off" time as determined by the study investigator during 8-hour clinic visits and 2) change in "off" time as determined by subjects' home motor diaries.

Sixty-five of the 83 enrolled subjects completed the study; withdrawal rates were equally distributed across treatment arms. KW-6002 treatment was significantly more effective than placebo treatment in reducing the proportion of awake time that patients spent in an "off" state. As assessed by home diaries, subjects assigned to KW-6002 experienced a reduction in the proportion of awake time spent in the OFF state of 7.1% compared to an increase of 2.2% in the placebo group (p=0.008). There was a 1.7 hour greater reduction in OFF time in the KW-6002 group than the placebo group (p=0.004). Results for the investigators' on/off 8 hour evaluation approached statistical significance (p=0.054). Patients treated with KW-6002 spent 0.51 fewer hours in the "off" state than did patients in the placebo group (p=0.061).

The study also showed a reduction in early morning dystonia in patients treated with KW-6002 from baseline to Week 12 compared to the placebo group.

Methods

This was a 12-week, double-blind, placebo-controlled, randomized, parallel group, multicenter, exploratory study of the safety and efficacy of KW-6002 as adjunctive therapy in L-DOPA-treated PD patients with motor complications. Eligible patients were those who met United Kingdom PD Society (UKPDS) brain bank diagnostic criteria (Daniel et al. (1993)), had been on L-DOPA/carbidopa for at least one year, were taking at least four doses of L-DOPA/carbidopa per day, and were experiencing motor complications including end-of-dose wearing off.

After providing informed consent, subjects underwent a screening period of four to eight weeks. Medications were stabilized prior to the week-4 visit. At this visit, the subjects received training regarding completion of home diaries.

At baseline, subjects underwent an 8-hour in-office evaluation. Subjects withheld PD medications and fasted from midnight prior to this evaluation. The first doses of PD medications for the day were administered after the initial assessments, and subsequent doses were administered at subjects' usual interdose intervals. Evaluations were performed by blinded raters who had undergone specific training and who were blinded to adverse events and results of laboratory tests. Subjects were required to exhibit at least 90 minutes of OFF time following PD medication administration during the 8-hour evaluation to be eligible for randomization.

Subjects who successfully completed screening and baseline evaluations were randomized to one of two dose regimens of KW-6002 or matching placebo in a 1:1:1 ratio. Patients randomized to KW-6002 received either 5 mg/day during weeks 1-4, 10 mg/day during weeks 5-8, and 20 mg/day during weeks 9-12 (5/10/20 group) or 10 mg/day during weeks 1-4, 20 mg/day during weeks 5-8, and 40 mg/day during weeks 5-9 (Oct. 20, 1940 group). (FIG. 1). Study medication was taken daily as a single dose with the subjects' normal breakfast.

Subsequent evaluations were undertaken at 2, 4, 6, 8, 10, and 12 weeks. Subjects completed three daily home diaries during the week before each visit. At each visit, adverse events were assessed. Eight-hour in-office evaluations were completed at weeks 4, 8, and 12. Laboratory blood tests and ECGs were obtained at baseline and weeks 4, 8, and 12.

During the course of the study, investigators could decrease the total daily dose of L-DOPA to ameliorate L-DOPA-related adverse events. Changes in the interval between L-DOPA doses were not permitted.

Results

Eighty-three subjects underwent randomization.

No notable differences of demographic and baseline characteristics were found among the study groups.

Subjects in all three treatment groups were 99% compliant with their study medication based on pill counts. During the study, there were no significant changes in mean daily L-DOPA doses in any treatment group or comparing combined KW-6002 and placebo groups.

Subjects randomized to KW-6002 experienced a significant decrease in OFF time compared to subjects randomized to placebo as assessed by home diaries (FIG. 1). Subjects assigned to KW-6002 experienced a reduction in the proportion of awake time spent in the OFF state of 7.1% compared to an increase of 2.2% in the placebo group (p=0.008). Both KW-6002 dose groups exhibited a significant decrease in percent OFF time compared to the placebo group. Similarly, the combined KW-6002 group, as well as each KW-6002 group, experienced a significant reduction in total hours OFF. Subjects assigned to KW-6002 experienced a reduction in OFF time of 1.2 hours compared to an increase of 0.5 hours in the placebo group (p=0.004) (FIG. 1).

Assessment of OFF time by investigators during 8-hour in-office evaluations identified a trend for greater reduction in OFF time in the combined KW-6002 group compared to the placebo group. Subjects assigned to KW-6002 exhibited a 10.0% decrease in OFF time compared to a decrease of 3.3% in the placebo group (p=0.05). Similarly, subjects assigned to KW-6002 exhibited a decrease in OFF time of 0.8 hours compared to a decrease of 0.3 hours in the placebo group (p=0.06). Off time reduction at the higher dose KW-6002 group was significant (P=0.02).

Early morning dystonia in patients treated with KW-6002 was reduced from baseline to Week 12 compared to the placebo group.

The overall adverse event profile was of no difference in subjects treated with KW-6002 versus placebo. The overall occurrence of serious adverse events was similarly distributed across the study groups. The number of total withdrawals and withdrawals due to adverse events were similar in the KW-6002 and placebo groups. No notable changes or differences between KW-6002 and placebo groups were observed in systolic or diastolic blood pressure, heart rate, respiratory rate, body weight, ECG, and mean values urinalysis or blood chemistry analyses remained within laboratory reference range.

In this study, under a variety of concomitant medication with dopamine agonists (e.g., Pramipexol, Pergolide, Ropinirol, Bromocriptine), COMT inhibitors (e.g., Entacapone, Tolcapone) and a MAO inhibitor selegiline, KW-6002 showed significant OFF time reduction, and safety and good tolerability.

Based on the findings of this study, the adenosine $A_{2A}$ receptor antagonist KW-6002 can safely and effectively reduce off time in Parkinson's disease patients with L-DOPA motor complications.

The present study also shows that the adenosine $A_{2A}$ receptor antagonist KW-6002 showed significant OFF time reduction in Parkinson's disease patients treated with the concomitant medication of L-DOPA and a dopamine agonist and/or a COMT inhibitor and/or a MAO inhibitor.

The present study also shows that KW-6002 reduces early morning dystonia in Parkinson's disease patients.

Although the foregoing invention has been described in some detail by way of illustration and example for purposes of clarity and understanding, it will be apparent to those skilled in the art that certain changes and modifications may be practiced. Therefore, the description and examples should not be construed as limiting the scope of the invention.

EXAMPLE 2

Sixteen individuals with moderate to advanced Parkinson's disease consented to participate in this double-blind, placebo-controlled study. All were randomized to either KW-6002, or matching placebo capsules. The study employed a rising dose design (40 and 80 mg/day) lasting 6 weeks. Parkinsonism was rated on the UPDRS part III Motor Examination. All evaluations were videotaped for subsequent off-line scoring by a second, blinded rater.

KW-6002 alone or in combination with a steady-state intravenous infusion of each patient's optimal L-DOPA dose had no effect on Parkinsonian severity. At a threshold dose of infused L-DOPA, KW-6002 potentiated the antiparkinsonian response by 38% (p<0.05). No medically significant drug toxicity was observed.

KW-6002 in combination with a threshold dose of L-DOPA improved motor condition (rated using the UPDRS III Motor Examination scale) items as much as the optimal L-DOPA dose alone.

Thus, the present invention provides methods and compositions for treating Parkinson's disease patients with a sub-clinically effective dose of L-DOPA by combining L-DOPA treatment with an effective amount of one or more adenosine $A_{2A}$ receptor antagonists (i.e., L-DOPA sparing effect).

The study showed that mean scores for tremor at rest and rise from chair demonstrated substantial improvement at Weeks 4 and 6 with respect to baseline and the placebo group. Mean scores for gait and body bradykinesia were observed to appreciably improve in KW-6002-treated patients at Week 6, relative to baseline and the placebo treated group. This means that KW-6002 also effectively treats tremor and gait of both Parkinson's disease patients and patients having other movement disorders.

Thus, the present invention provides methods for the effective treatment of movement disorders with tremor, bradykinesias, gait and bradykinesia.

The findings derived from Examples 1 and 2 confirm that adenosine $A_{2A}$ receptor mechanisms play a role in symptom production in Parkinson's disease and motor complications, and that drugs able to block the receptors selectively confer therapeutic benefit to L-DOPA treated patients with this disorder.

That is, the present invention provides methods of treating movement disorders by administering an effective amount of one or more adenosine $A_{2A}$ receptor antagonists to a patient in need thereof, as well as methods of reducing or suppressing the adverse effectiveness of L-DOPA in patients receiving L-DOPA therapy in the treatment of Parkinson's disease.

EXAMPLE 3

GABA and glutamate concentrations in an output nucleus of basal ganglia, substantia nigra pars reticulata (SNr), are measured in the 6-hydroxydopamine lesion rats and the chronically L-DOPA-treated rats after 6-hydroxydopamine lesion. Effect of adenosine $A_{2A}$ receptor selective antagonists on GABA and glutamate levels in SNr and dyskinesias was examined.

Methods:

6-hydroxydopamine (8 μg) was injected into the left medial forebrain bundle in a rat. One week after the lesion, the rats were then tested for contralateral turning by injecting apomorphine (0.1 mg/kg s.c.). Only those animals showing robust contralateral turning were used in subsequent experiments. Three days after the apomorphine tests, L-DOPA was administrated orally twice a day at a dose of 20 mg/kg for 1 to 3 weeks.

For qualification of L-DOPA induced dyskinesia, rats were observed individually to score severity scale of abnormal involuntary moments (AIM) including locomotive, axial, limb and orolingual AIMs, which assigns a score from 0 to 4 to each of the four AIM subtypes according to the proportion of time/monitoring period during which the AIM is present. During the chronic treatment of L-DOPA, recording of severity scale of AIMs were carried out. In addition, an amplitude-based scale for each limb and axial AIMs was scored during a microdialysis study. Amplitude scores of limb or axial AIMs (each ranging from 0 to 4) was rated based on both the magnitude of paw/limb translocation and of the visible involvement of distal versus proximal muscle groups or on the lateral deviation (or torsion) of an animal's neck and trunk from the longitudinal axis of its body, respectively.

GABA and glutamate in SNr were measured after 6-hydroxydopamine lesion and four days after terminating the repeated L-DOPA treatments, with in vivo microdialysis technique. Rats were placed in each test chamber and the microdialysis probe inserted into SNr was attached to a fluid swivel (TCS2-23, Eicom) that allowed free movement (also sustained rotational behavior). Probes were continuously perfused with a modified Ringer's solution (1.2 mmol/L $CaCl_2$, 2.7 mmol/L KCl, 148 mmol/L NaCl, and 0.85 mmol/L $MgCl_2$; pH 7, artificial cerebrospinal fluid solution) at a rate of 2 µL/min via a microinjection pump (CMA/100, Carnegie Medicin AB). After stabilization of basal level of release for 3-4 h, 4 samples (60 µL each) during 2 h of perfusion were collected using a fraction collector (CMA/140, Carnegie Medicin). Sixty µL of perfusate per sample (during 30 min) was divided into 2×30 µL in sampling tubes (sample vial for Auto-sampling-injector 231XL, Eicom), and the concentrations of GABA and glutamate were determined from each sample. The samples were immediately assayed or frozen and stored in a deep freeze (−80° C.) before assays. GABA and glutamate were analyzed using reverse phase high-performance liquid chromatograph with fluorescence detection after pre-column derivatization of the amino acids with orthophthaldialdehyde reagent. Lindroth and Mopper (1979).

Figure 2A:
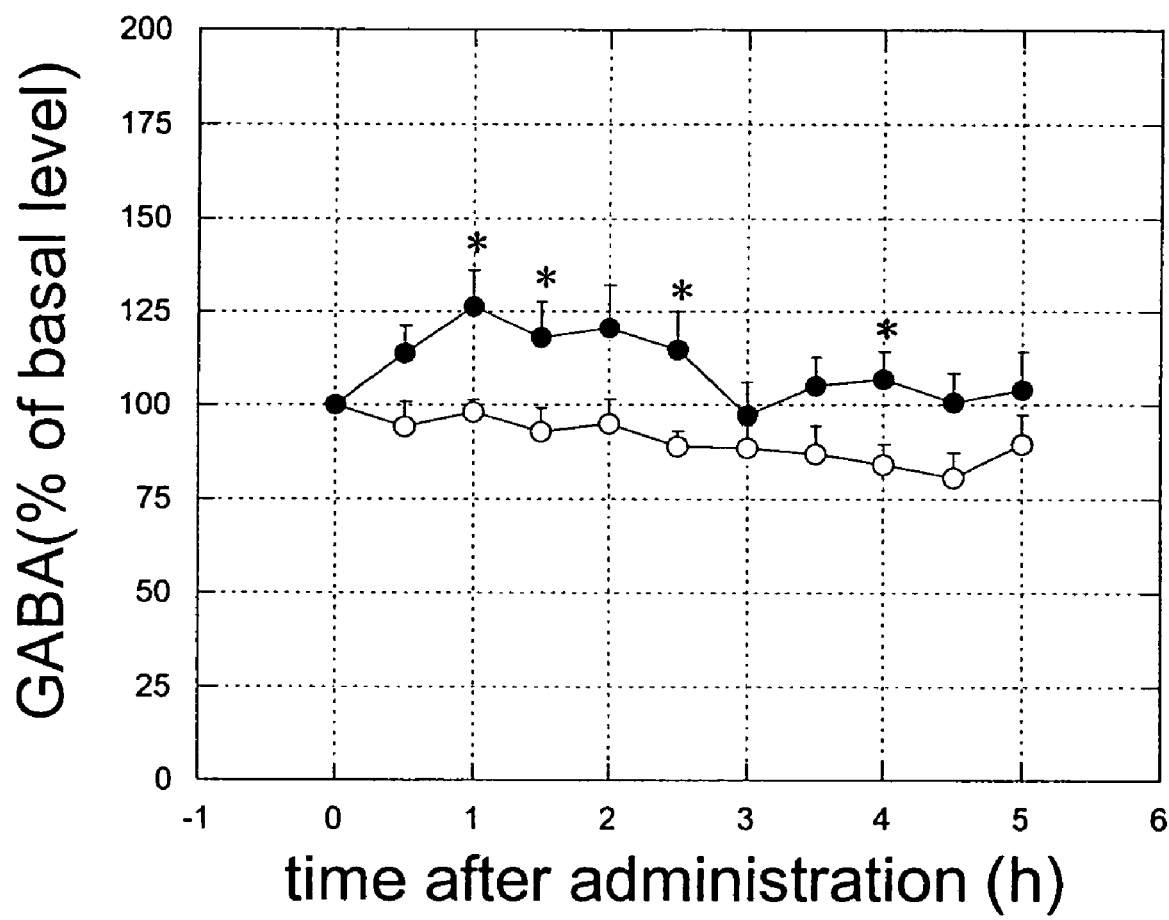
FIG. 2 is a graph depicting the effect of KW-6002 on nigral GABA (2A) and glutamate (2B) levels in 6-hydroxydopamine lesion rats. GABA and glutamate levels are expressed as percentage changes from the pre-values before administration of the compound. KW-6002 at 1 mg/kg p.o. significantly increased nigral GABA and glutamate levels.
Figure 2B:
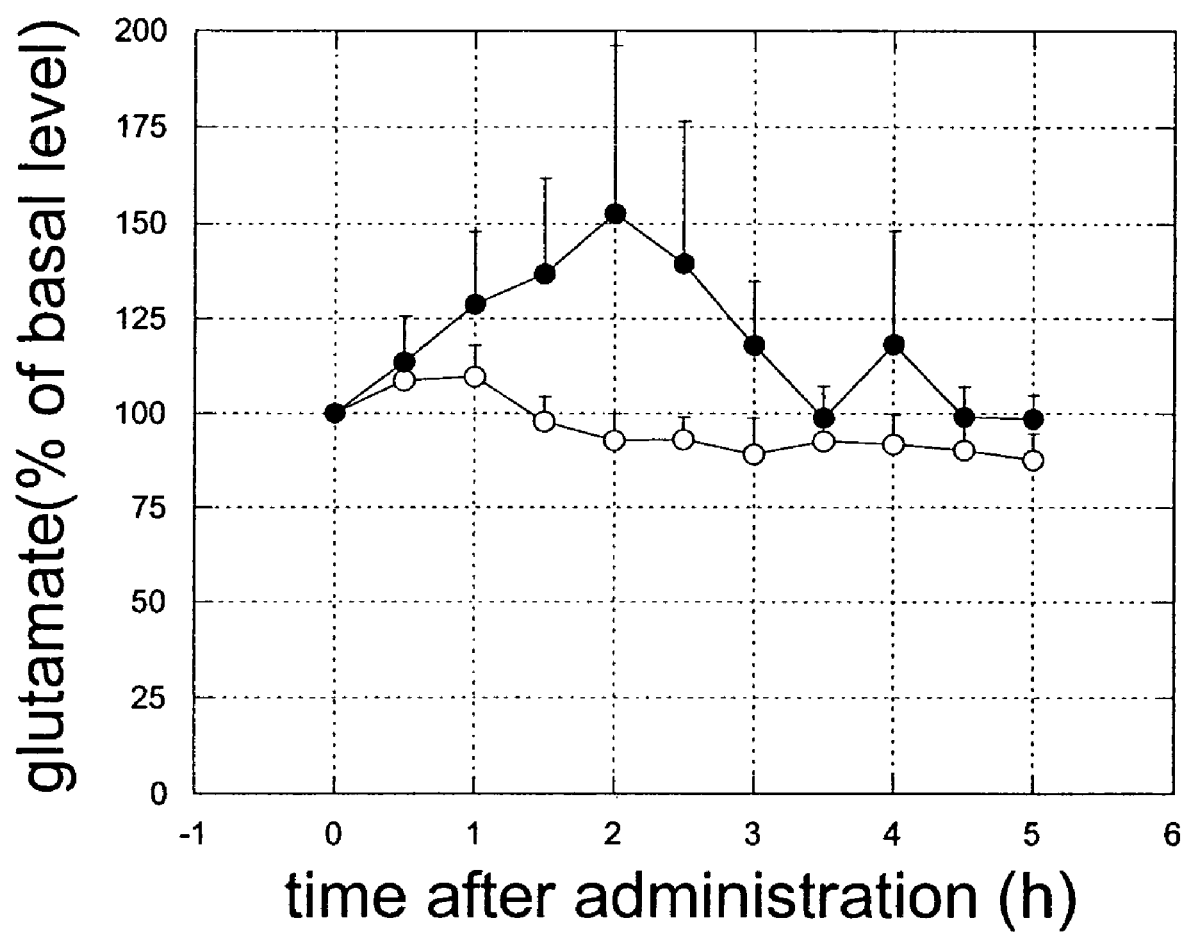
Figure 3A:
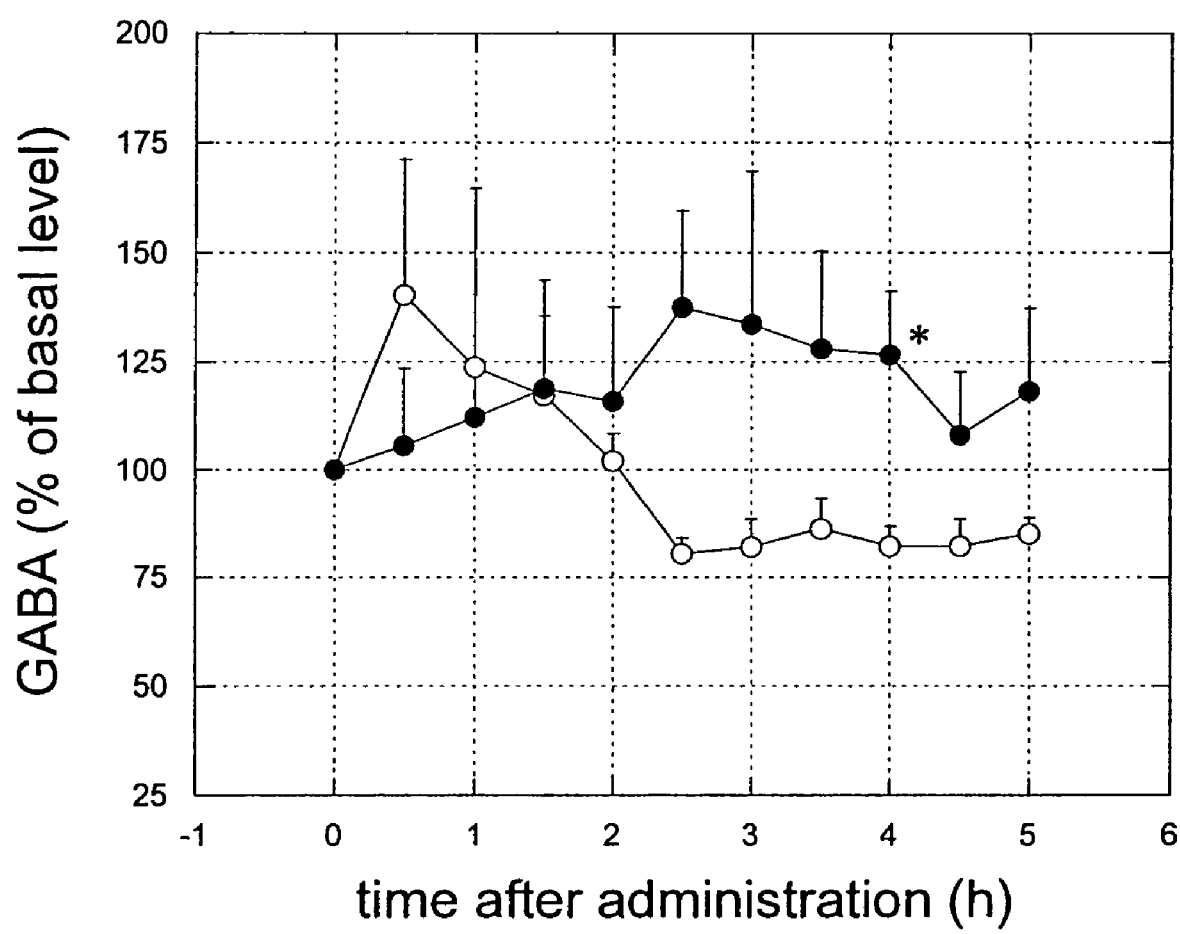
FIG. 3 is a graph depicting the effect of L-DOPA on nigral GABA (3A) and glutamate (3B) levels in 6-hydroxydopamine lesion rats. L-DOPA induced significant increases of nigral GABA and glutamate to levels similar to those by KW-6002.
Figure 3B:
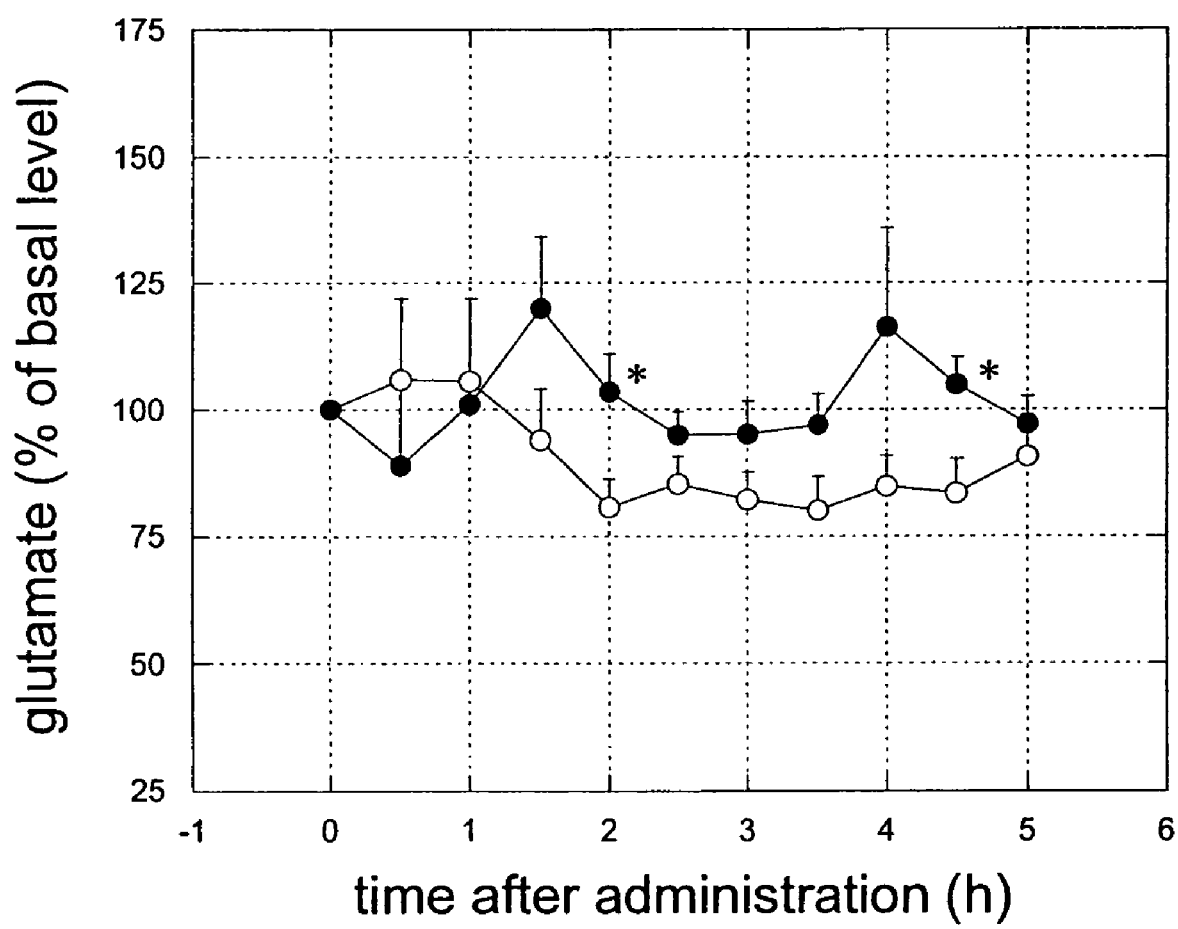

Results:

KW-6002 (1 mg/kg p.o.) caused a marked and sustained increase of GABA and glutamate levels in the SNr of the 6-hydroxydopamine lesioned rats (FIG. 2A, 2B). L-DOPA also induced the facilitation of nigral GABA and glutamate in 6-hydroxydopamine lesioned rats (FIG. 3A, 3B)

AIMs with 1 week daily repeated treatments of L-DOPA were still varied in individual rat and maintained the maximum severity grades for a short time. With 2 to 3 weeks in chronic L-DOPA treatments, animals produced stable AIMs, and maintained average maximum AIM scores (9) from 10 min to 3 hrs after L-DOPA administration.

The basal nigral glutamate concentration maintained constant levels until 2 week chronic treatment of L-DOPA, and drastically increase in 3 weeks, whereas nigral GABA levels maintained unchanged throughout the periods, as shown in Table 3. Table 3 shows the basal level of nigral GABA and glutamate in chronic L-DOPA-treated rats after 6-hydroxydopamine lesion.

TABLE 3

| | Duration of L-DOPA treatment | | | |
|---|---|---|---|---|
| | 0 | 1 week | 2 weeks | 3 weeks |
| GABA, nmol/L (N) | 19.8 ± 2.5 (11) | 19.3 ± 2.3 (3) | 20.9 ± 6.8 (3) | 23.6 ± 4.5 (13) |
| Glutamate, nmol/L (N) | 185.0 ± 36.5 (12) | 147.5 ± 38.1 (3) | 112.0 ± 47.1 (3) | 425.4 ± 99.6 (13) |

Figure 4:
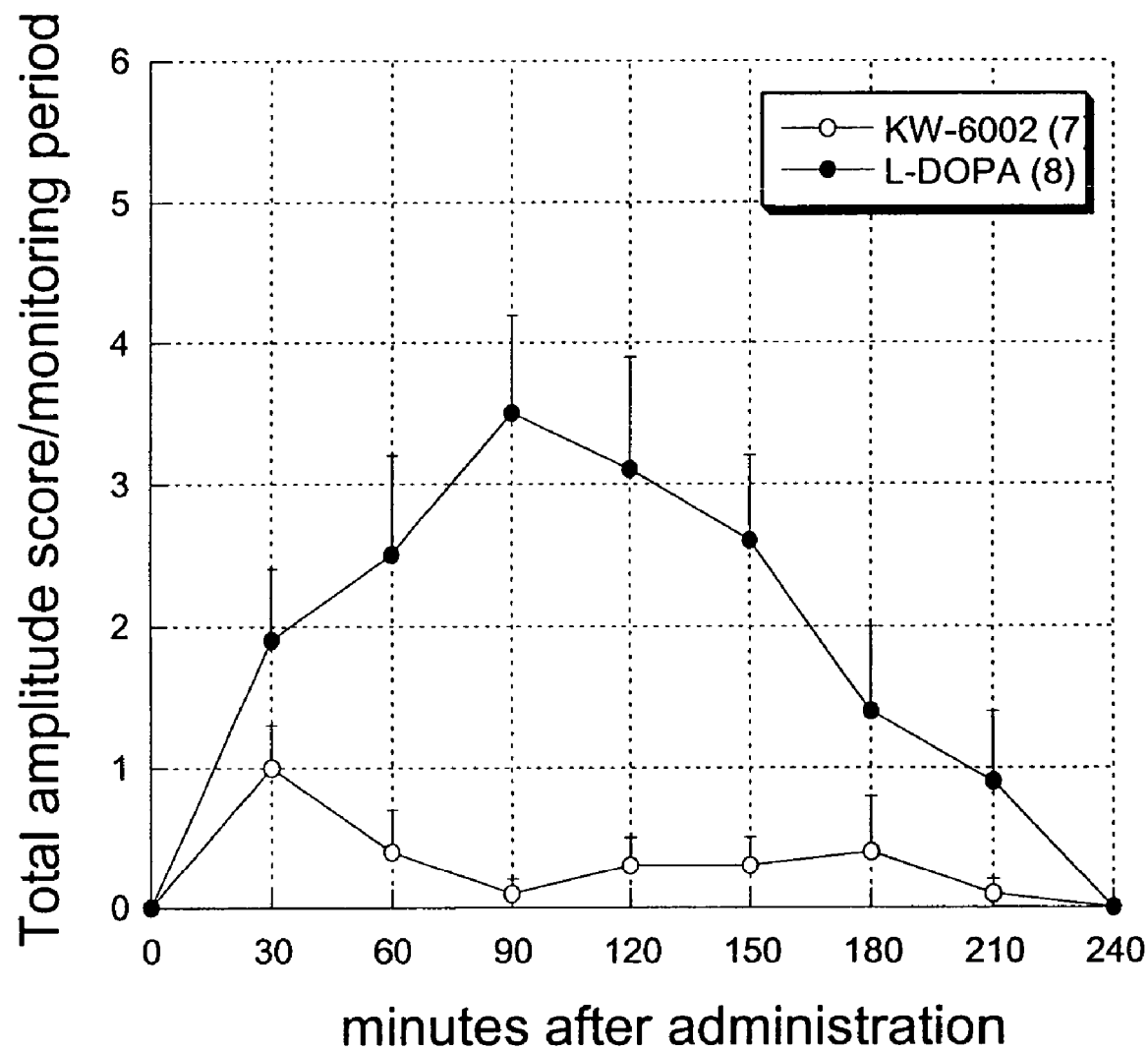
FIG. 4 is a graph depicting the time courses of the effect of KW-6002 and L-DOPA on total abnormal involuntary movements (AIMs) score in chronically L-DOPA-treated 6-hydroxdopmanine lesion rats. L-DOPA elicited marked AIMs, whereas KW-6002 induced little or no AIMs.

L-DOPA elicited marked AIMs (sum of the amplitude score of limb and axial AIMs), whereas KW-6002 induced little or no AIMs in the chronically treated rats (FIG. 4).

L-DOPA increased glutamate levels without effect on nigral GABA levels, whereas KW-6002 gave no or little effects on nigral GABA and glutamate levels (FIG. 5).

The time courses of increase of L-DOPA induced AIMs amplitude were parallel with the increase of L-DOPA induced nigral glutamate levels (FIGS. 4 and 5B).

EXAMPLE 4

To compare in MPTP monkeys rendered parkinsonian by repeated injections of MPTP and having never received L-DOPA or dopaminergic agents the effect of chronic treatment with L-DOPA alone or in combination with KW-6002 or placebo.

ANIMALS: 8 (eight) female drug-naïve cynomologus monkeys weighing between 3 and 5 kg were used. They were rendered parkinsonian by subcutaneous infusion of MPTP (0.5 mg daily) until development of an obvious parkinsonian Syndrome (akinesia, hunched posture and tremor associated with a disability score on our scale of 6 or more). The cumulative dose necessary was variable: from 3.5 to 23.5 mg.

The animals were allowed to recover during at least one month except an animal who had to be treated earlier because of marked akinesia. They were scored at least once daily. The disability score remained stable throughout that period.

TREATMENT: All animals were treated with L-DOPA/benserazide 100/25 mg (total dose) once daily. The drug was administered orally with a special capsule handler. The animals in the KW-6002 group also received this compound (90 mg/kg) by the oral route. The animals were observed daily (from Monday to Friday) in their cages through a one-way screen and video recordings were made of significant events (abnormal behavior—dyskinesias). They were scored on disability scale and eventually dyskinesia rating scale, before and during the effect. The treatment with L-DOPA was continued for one month.

Results

Figure 6:
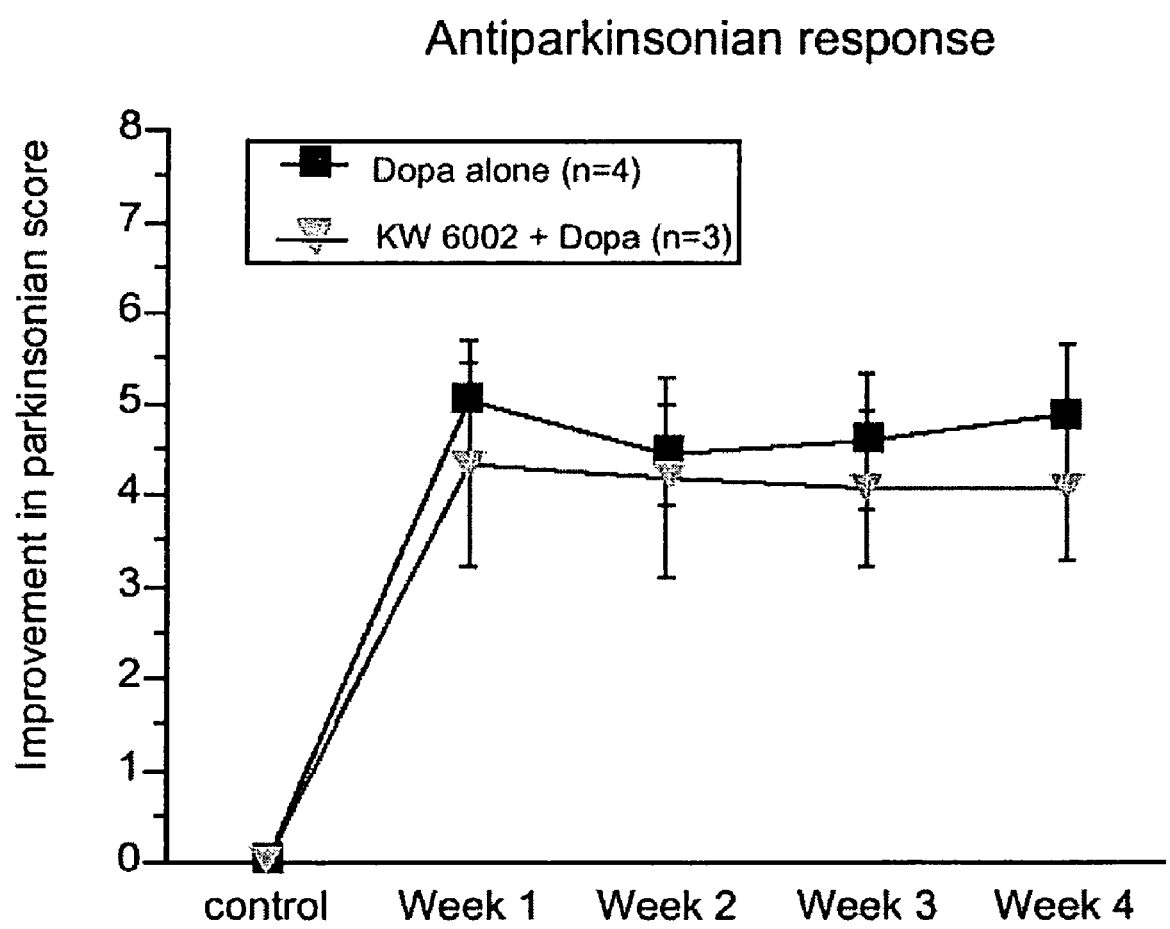
FIG. 6 is a graph depicting the effect of KW-6002 on antiparkinsonian response to L-DOPA during the treatment L-DOPA alone (L-DOPA/benserazide; 100/25 mg (total dose) once daily) and L-DOPA plus KW-6002 (90 mg/kg once daily) in cynomolgus monkeys. The antiparkinsonian response to L-DOPA in terms of improvement of the parkinsonian score over four weeks in was stable and comparable in the two groups.

The antiparkinsonian response to L-DOPA in terms of improvement of the parkinsonian score over four weeks was stable and comparable in the L-DOPA alone group and in the combination (L-DOPA+KW-6002) treatment group. (FIG. 6).

Figure 7:
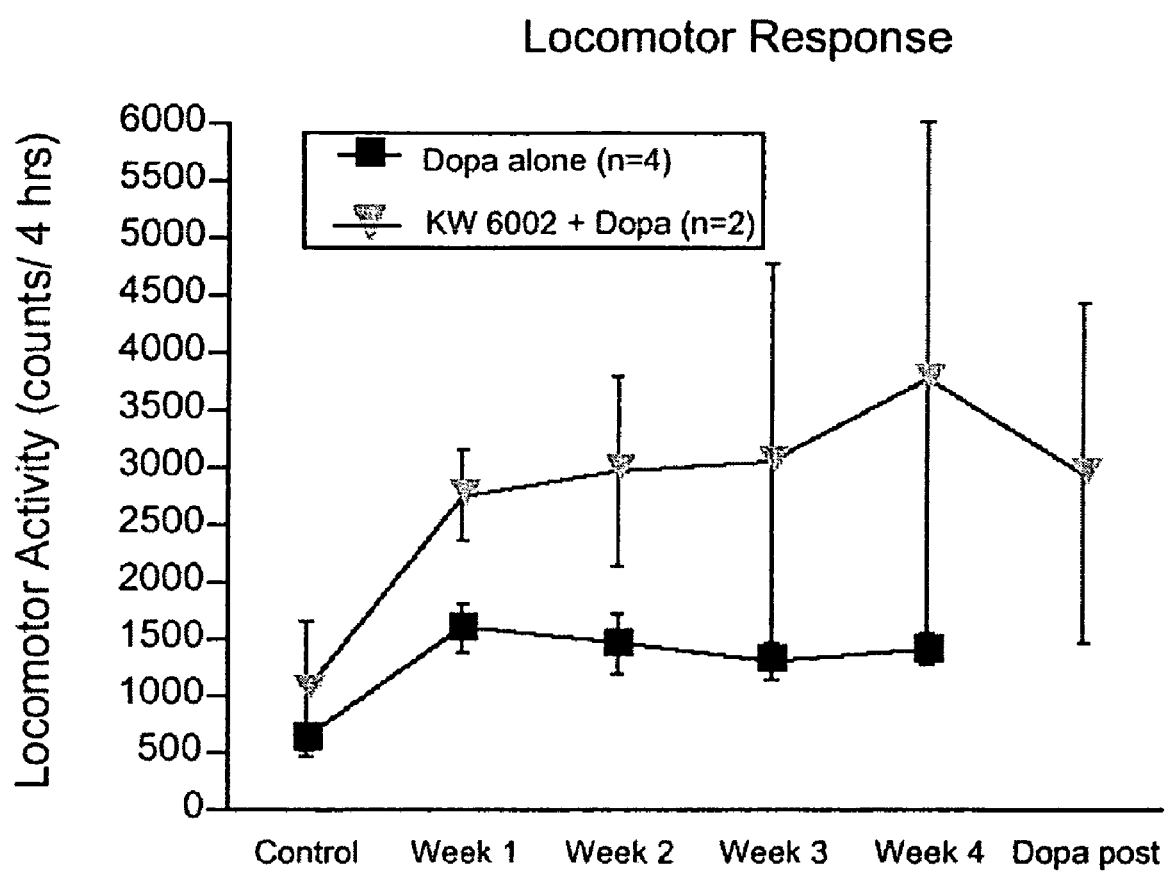
FIG. 7 is a graph depicting the effect of KW-6002 on Locomotor response to L-DOPA during the treatment L-DOPA alone (L-DOPA/benserazide; 100/25 mg (total dose) once daily) and L-DOPA plus KW-6002 (90 mg/kg once daily) in cynomologus monkeys. The locomotor activity counts increased to a higher level in the combination treatment group and its level was maintained over four weeks.

The locomotor activity counts increased to a higher level in the combination treatment group and its level was maintained over four weeks. (FIG. 7).

Figure 8:
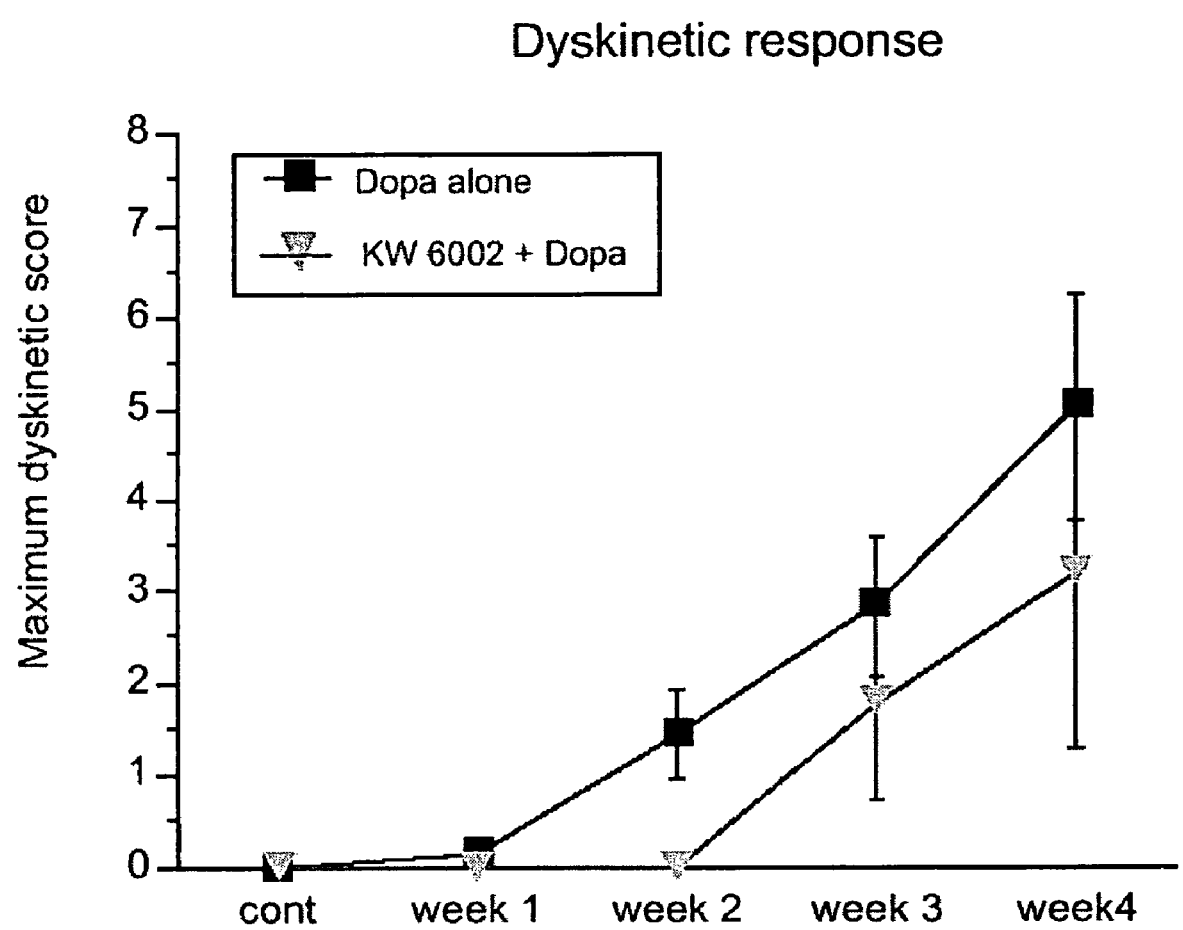
FIG. 8 is a graph depicted the effect of KW-6002 on dyskinetic response to L-DOPA during the treatment L-DOPA alone (L-DOPA/benserazide; 100/25 mg (total dose) once daily) and L-DOPA plus KW-6002 (90 mg/kg once daily) in cynomologus monkeys. Dyskinesias increased more rapidly and reached a higher level in the L-DOPA group than in the combination treatment group. The onset of dyskinesia was delayed in the presence of KW-6002.

Dyskinesias increased more rapidly and reached a higher level in the L-DOPA group than in the combination treatment group. Thus, the onset of dyskinesia was delayed in the presence of KW-6002. Even after appearance of dyskinesia (week 3 and 4), the KW-6002 treatment group produced less dyskinesia than L-DOPA alone group. (FIG. 8).

At the end of the one-month treatment period, all drugs were stopped. The following day, the animals of the KW-6002 group were challenged with a standard dose of L-DOPA/benserazide(100/25 mg), administered orally. The three animals that had already displayed dyskinesias had a similar response to the combination.

In conclusion, the addition of KW-6002 to L-DOPA in the treatment of previously drug-naïve parkinsonian monkeys during one month delay the onset of dyskinesia and produced less dyskinesia, while it produced stronger locomotor response, and a similar improvement of the parkinsonian score.

EXAMPLE 5

Effect of KW-6002 on L-DOPA induced dyskinesia in MPTP treated common marmosets that had previously been primed to exhibit dyskinesia L-DOPA was investigated.

METHODS: MPTP (Sigma-Aldrich, St. Louis, Mo., USA) was dissolved in physiological saline and administered at a dose of 2.0 mg/kg s.c daily for 5 days. Then, MPTP 2 mg/kg were further administered approximately 3 weeks. 8 weeks after exposure to MPTP, animals showed chronic parkinsonian symptoms such as marked reduction of basal locomotor activity, slower and less coordinated movements, abnormal postures of some parts of the body, and reduced checking movement and eye blinks. The animals, which showed sufficient chronic parkinsonian symptoms, were selected for this study.

L-DOPA (10 mg/kg p.o.) plus benserazide (2.5 mg/kg p.o.) was then administered twice daily for 28 days to the MPTP-treated marmosets to induce dyskinesia. The dyskinesia of the animals was scored using the rating scale described in Table 4. The animals, which showed high dyskinesia score up to 8 by each L-DOPA administration, were used in this study. Dyskinesias induced by L-DOPA (10 mg/kg p.o. plus benserazide 2.5 mg/kg p.o.) were scored in MPTP-treated marmosets. The score was calculated as the L-DOPA pre value. On the next day the animals received vehicle for the vehicle control value. One day later, they were administered with L-DOPA (2.5 mg/kg, p.o.) to obtain the L-DOPA control value. Then the effects of KW-6002 on L-DOPA induced dyskinesia were observed. Administration of KW-6002 (10 mg/kg p.o.) combined with L-DOPA (2.5 mg/kg, p.o.) was started on the following day (day 1) and repeated once daily for 21 days, followed by a one-week washout period. Animals were assessed for dyskinesia on days 1, 3, 5, 7, 14, 21 and 28 according to the rating scale. In addition, the L-DOPA post value was obtained by administration of L-DOPA (10 mg/kg p.o.) to the marmosets on day 35.

Table 4 shows the results of quantifying the presence of limb dystonia, chorea and choreathetoid dyskinesia and stereotypies. Abnormal movement such as, orofacial movements, myoclonus and complex stereotypic behaviors (e.g., elaborate checking, obsessive grooming), are exclude from dyskinesia rating.

TABLE 4

| Score | | |
|---|---|---|
| 0 | Absent | |
| 1 | Mild | Fleeting and rare dyskinetic postures and movements. |
| 2 | Moderate | More prominent abnormal movements, but not interfering significantly with normal behavior. |
| 3 | Marked | Frequent and at times continuous dyskinesias intruding upon normal repertory of activity. |
| 4 | Severe | Virtually continuous dyskinetic activity, disabling to animal and replacing normal behavior. |

Remarks according to dyskinesia.
Dystonia (arm, leg and trunk): abnormal sustained posture (ex. leg elevation).
Stereotypic reaching (arm)
Athetosis (arm and leg): writhing twisting movements.
Chorea (arm and leg): abnormal rapid (dance like) movements of limbs.
Akathisia: motor restlessness.
Dyskinesia score is become higher according to severity of dyskinesia. The maximal score is four points.

Figure 9:
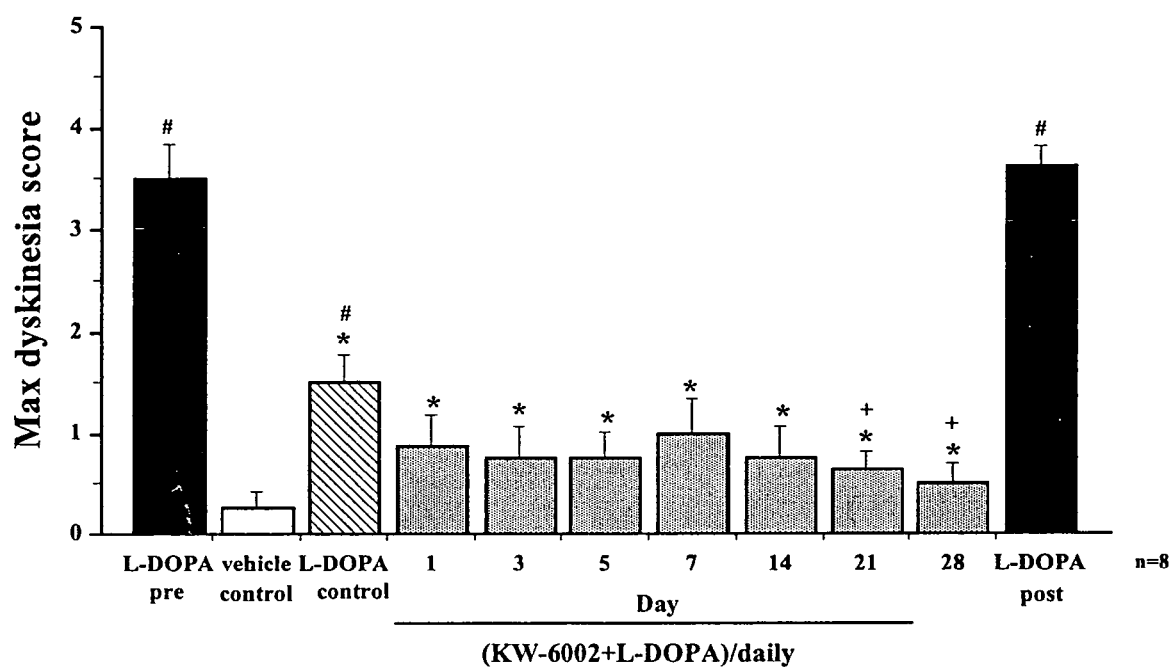
FIG. 9 is a graph depicted the effect of KW-6002 on L-DOPA induced dyskinesias. KW-6002 was administered simultaneously when L-DOPA (2.5 mg/kg p.o. plus benserazide 0.625 mg/kg p.o.) was administered daily for 21 days to induce dyskinesia in MPTP-treated common marmosets primed with L-DOPA to exhibit dyskinesia. The animals previously received 28 days of L-DOPA at 10 mg/kg p.o. plus benserazide at 2.5 mg/kg p.o. twice daily (L-DOPA). The amplitude of involuntary movements produced by the combined treatment was not increased, but instead reduced significantly on day 21 as compared with 2.5 mg/kg of L-DOPA alone.

RESULTS: Results was represented on FIG. 9. Oral administration of L-DOPA (2.5 mg/kg) induced mild dyskinesias in MPTP-treated common marmosets that had previously been primed to exhibit dyskinesia by L-DOPA. The L-DOPA (2.5 mg/kg p.o.) induced dyskinesia was not changed or trended to reduced by KW-6002 (10 mg/kg p.o.) for 21 days compared with L-DOPA alone control. On the day 21, KW-6002 shows significant reduction of L-DOPA induced dyskinesias compared with 2.5 mg/kg of L-DOPA alone. The significant reduction caused by KW-6002 in L-DOPA induced dyskinesia was observed by acute administration of KW-6002 (10 mg/kg) with L-DOPA (2.5 mg/kg) in 1 week after the repeated administration for 21 days of KW-6002 and L-DOPA.

In conclusion, results of these experiments indicate that KW-6002 suppresses L-DOPA induced dyskinesias.

Preparation Example 1

Tablets

Tablets having the following composition are prepared in a conventional manner.

KW-6002 (40 g) is mixed with 286.8 g of lactose and 60 g of potato starch, followed by addition of 120 g of a 10% aqueous solution of hydroxypropyl cellulose. The resultant mixture is kneaded, granulated, and then dried by a conventional method. The granules are refined to give granules used to make tablets. After mixing the granules with 1.2 g of magnesium stearate, the mixture is formed into tablets each containing 20 mg of the active ingredient by using a tablet maker (Model RT-15, Kikusui) having pestles of 8 mm diameter.

The prescription is shown in Table 5.

TABLE 5

| | |
|---|---|
| Compound (I) | 20 mg |
| Lactose | 143.4 mg |
| Potato Starch | 30 mg |
| Hydroxypropyl Cellulose | 6 mg |
| Magnesium Stearate | 0.6 mg |
| | 200 mg |

Preparation Example 2

Capsules

Capsules having the following composition are prepared in a conventional manner.

KW-6002 (200 g) is mixed with 995 g of Avicel and 5 g of magnesium stearate. The mixture is put in hard capsules No. 4 each having a capacity of 120 mg by using a capsule filler (Model LZ-64, Zanashi) to give capsules each containing 20 mg of the active ingredient.

The prescription is shown in Table 6.

TABLE 6

| | |
|---|---|
| Compound (I) | 20 mg |
| Avicel | 99.5 mg |
| Magnesium Stearate | 0.5 mg |
| | 120 mg |

Preparation Example 3

Injections

Injections having the following composition are prepared in a conventional manner.

KW-6002 (1 g) is dissolved in 100 g of purified soybean oil, followed by addition of 12 g of purified egg yolk lecithin and 25 g of glycerin for injection. The resultant mixture is made up to 1,000 ml with distilled water for injection, thoroughly mixed, and emulsified by a conventional method. The resultant dispersion is subjected to aseptic filtration by using 0.2 μm disposable membrane filters, and then aseptically put into glass vials in 2 ml portions to give injections containing 2 mg of the active ingredient per vial.

The prescription is shown in Table 7.

TABLE 7

| Compound (I) | 2 mg |
|---|---|
| Purified Soybean Oil | 200 mg |
| Purified Egg Yolk Lecithin | 24 mg |
| Glycerine for Injection | 50 mg |
| Distilled Water for Injection | 1.72 ml |
| | 2.00 ml |

Although the foregoing invention has been described in some detail by way of illustration and example for purposes of clarity and understanding, it will be apparent to those skilled in the art that certain changes and modifications may be practiced. Therefore, the description and examples should not be construed as limiting the scope of the invention.

REFERENCE LIST

U.S. Pat. No. 5,484,920
U.S. Pat. No. 5,543,415
U.S. Pat. No. 5,587,378
Adler et al. (1993a) "Vitamin E treatment of tardive dyskinesia" Am. J. Psych. 150:1405-1407
Adler et al. (1993b) "Vitamin E in tardive dyskinesia: time course of effect after placebo substitution" Psychopharmacol. Bull. 29:371-374
Adler et al. (1999) "Vitamin E treatment for tardive dyskinesia" Arch. Gen. Psych. 56:836-841
Akhtar et al. (1993) "Vitamin E in the treatment of tardive dyskinesia" J. Neural. Transm. Gen. Sect. 92:197-201
Alexander et al. (1990) "Functional architecture of basal ganglia circuits: neuronal substrates of processing" Trends Neurosci. 13:266-271
American College of Neuropsychopharmacology-FDA Task Force (1973) "Neurologic syndromes associated with neuroleptic drug use" N. Engl. J. Med. 289:20-23
Aoyama et al. (2000) "Rescue of locomotor impairment in dopamine $D_2$ receptor-deficient mice by an adenosine $A_{2A}$ receptor antagonist" J. Neurosci. 20:5848-5852
Aoyama et al. (2002) "Distribution of adenosine $A_{2A}$ receptor antagonist KW-6002 and its effect on gene expression in the rat brain" Brain Res. 953:119-25
Arvidsson et al. (1997) J. Comp. Neurol. 378:454-467
Augood et al. (1994) "adenosine $A_{2A}$ receptor mRNA is expressed by enkephalin cells but not by somatostatin cells in rat striatum: co-expression study" Mol. Brain Res. 22:204-210
Baik et al. (1995) "Parkinsonian-like locomotor impairment in mice lacking dopamine $D_2$ receptors" Nature 377:424-428
Baldessarini and Tarsy (1978) "Tardive dyskinesia" In: Psychopharmacology: a generation of progress. Lipton et al. eds. NY Raven Press pp. 995-1004
Baldessarini (1990) "Drugs and the treatment of psychiatric disorders" Goodman and Gilman's The Pharmacological Basis of Therapeutics, Gilman et al. (eds). New York, Pergamon Press, 8th Ed pp. 383-435
Bartholini (1983) "GABA system, GABA receptor agonist and dyskinesia" In: Modern problems in pharmacopsychiatry. Ban et al. eds. New York: Karger 21:143-154
Bezard et al. (2001) "Pathophysiology of levodopa-induced dyskinesia: Potential for new therapies" Nature Neurosci. Rev. 577-588
Bischot et al. (1993) "Vitamin E in extrapyramidal disorders" J. Postgrad. Med. 39:124-126
Blurn and Korczyn (1983) "Peptide neurotransmitters and their implications for the treatment of tardive dyskinesia" In: Modern problems in pharmacopsychiatry. Ban et al. eds. New York: Karger 21:187-95
Brown et al. (1991) "Striatal $A_2$ receptor regulates apomorphine-induced turning in rats with unilateral dopamine denervation" Psychopharmacol. 103:78-82
Burns et al. (1986) "Characterization of the $A_2$ adenosine receptor labeled by [$^3$H]NECA in rat striatal membranes" Mol. Pharmacol. 29:331-346
Casey (1999) "Tardive dyskinesia and atypical antipsychotic drugs" Schizophrenia Res. 35:561-566
Chen et al. (2001a) J. Neurosci. 21:RC143(1-6)
Chen et al. (2001b) "The role of the $D_2$ dopamine receptor ($D_2$R) in $A_{2A}$ adenosine receptor ($A_{2A}$R)-mediated behavioral and cellular responses as revealed by $A_{2A}$ and $D_2$ receptor knockout mice" Proc. Natl. Acad. Sci. USA 98:1970-1975
Chergui et al. (2000) "Functional GluR6 kinase receptors in the striatum: indirect down-regulation of synaptic transmission" J. Neurosci. 20:2175-2182
Claveria et al. (1975) "Tardive dyskinesia treated with pimozide" J. Neurol. Sci.; 24:393-401
Cochiolo et al. (2000) J. Neuroscience Res. 59:126-135
Crossman (1990) "A hypothesis on the pathophysiological mechanisms that underlie levodopa or dopamine-agonist-induced dyskinesia in Parkinson's disease: implications for future strategies in treatment" Mov. Disord. 5:100-108
Dabiri et al. (1993) "Effectiveness of vitamin E for treatment of long-term tardive dyskinesia" Am. J. Psych. 150:1405-1407
Dabiri et al. (1994) "Effectiveness of vitamin E for treatment of long-term tardive dyskinesia" Am. J. Psych. 151:925-926
Daly et al. (1983) "Subclasses of adenosine receptors in the central nervous system: interaction with caffeine and related methylxanthines" Cell. Mol. Neurobiol. 3:69-80
Daniel et al. (1993) "Parkinson's disease society brain bank, London: overview and research" J. Neural Transm. 39(suppl): 165-172
DeLong (1990) "Primate model of movement disorders of basal ganglia origin" Trends Neurosci. 13:281-285
Dixon et al. (1996) "Tissue distribution of adenosine $A_{2A}$ receptor mRNAs in the rat" Bri. J. Pharmacol. 118: 1461-1468
Driesens (1988) "Neuroleptic medication facilitates the natural occurrence of tardive dyskinesia. A critical review" Acta-Psychiatr.-Belg. 88:195-205
Duvoisin (1974) "Variations in the 'on-off' phenomenon" Neurology 24:431-441
Egan et al. (1992) "Treatment of tardive dyskinesia with vitamin E" Am. J. Psych. 149:773-777
Egan et al. (1997) "Treatment of tardive dyskinesia" Schiz. Bull. 23:583-609
Elkashef et al. (1990) "Vitamin E in the treatment of tardive dyskinesia" Am. J. Psych. 147:505-506
Fahn et al. (1987) "Members of the UPDRS development committee. Unified Parkinson's disease rating scale" in: Fahn et al. eds., Recent developments in Parkinson's disease, Florham Park, N.J. Macmillan Health Care Information 2:153-163 and 293-304

Ferre et al. (1991) "Stimulation of adenosine A$_2$ receptors induces catalepsy" Neurosci Lett. 57:1062-1067

Ferre et al. (1996) "Dopamine D$_1$ receptor-mediated facilitation of GABAergic neurotransmission in the rat strioentopeduncular pathways and its modulation by adenosine A$_1$ receptor-mediated mechanisms" Eur. J. Neurosci. 8:1545-1553

Fink et al. (1992) "Molecular cloning of the rat A$_{2A}$ adenosine receptor: selective co-expression with D$_2$ dopamine receptors in rat striatum" Mol. Brain Res. 14:186-195

Florio et al. (1999) J. Pharmacol. Exp. Ther. 290:817-824

Fredholm et al. (1994) "Action of caffeine in the brain with special reference to dependence" Pharmacol. Rev. 46:143-156

Gardos et al. (1994) "Ten-Year outcome of tardive dyskinesia" Am. J. Psych. 151:836-841

Gelenberg et al. (1990) "A crossover study of lecithin treatment of tardive dyskinesia" J. Clin. Psych. 51:149-153

Gerfen et al. (1990) "D$_1$ and D$_2$ dopamine receptor-regulated gene expression of striatonigral and striatopallidal neurons" Science 250:1429-1432

Gerfen (1992) "The neostriatal mosaic: multiple levels of compartmental organization in the basal ganglia" Ann. Rev. Neurosci. 15:285-320

Goetz et al. (1994) "Utility of an objective dyskinesia rating scale for Parkinson's disease: inter- and intra-rater reliability assessment" Movement Dis. 9:390-394

Goldberg (1996) "The Use of Vitamin E to Treat People with Tardive Dyskinesia" J. Clin. Psych. 57:167-173

Graybiel (1990) "Neurotransmitters and neuromodulators in the basal ganglia" Trends Neurosci. 13:244-254

Grondin et al. (1999) "Antiparkinsonian effect of a new selective adenosine A$_{2A}$ receptor antagonist in MPTP-treated monkeys" Neurology 52:1673-1677

Groves (1983) "A theory of the functional organization of the neostriatum and the neostriatal control of voluntary movement" Brain Res. Rev. 5:109-132

Hoehn et al. (1967) "Parkinsonism: onset, progression and mortality" Neurol. 17:427-442

Hauser et al. (2000) "A home diary to assess functional status in Parkinson's disease patients with motor fluctuations and dyskinesia" Clin. Neuropharmacol. 23:75-81

Huang et al. (1981) "Reserpine and α-methyldopa in the treatment of tardive dyskinesia" Psychopharmacology 73:359-362

Hubble et al. (2002a) "Kyowa 6002-US-001 Study. Group. A novel adenosine antagonist (KW-6002) as a treatment for advanced Parkinson's disease (PD) with motor complications" Neurol. 54(suppl 6):S21.001

Hubble et al. (2002b) "A novel adenosine antagonist (KW-6002) as a treatment for advanced Parkinson's disease with motor complications" Neurol. 58(suppl 3):A162

Huntinger et al. (2001) "Ultrastructural localization of adenosine A$_{2A}$ receptors suggests multiple cellular sites for modulation of GABAergic neurons in rat striatum" J. Comparative Neurol. 431:331-356

Ikeda et al. (2002) "Neuroprotection by adenosine A$_{2A}$ receptor blockade in experimental models of Parkinson's disease" J. Neurochem. 80:262-270

Isaacson et al. (1995) "Counting quanta: direct measurements of transmitter release at a central synapse" Neuron 15:875-884

Itoh et al. (1981) "Drug-induced tardive dyskinesia" In: Current developments in psychopharmacology. Essman, Valzelli, eds. Jamaica, N.Y.: Spectrum 93-126

Jaeger et al. (1994) "Surround inhibition among projection neurons is weak or nonexistent in the rat neostriatum" J. Neurophysiol. 72:2555-2558

Jarvis et al. (1989) "Direct autographic localization of adenosine A$_2$ receptors in rat brain using the A$_2$ selective agonist [$^3$H]CGS21680" Eur. J. Pharmacol. 168:243-246

Kanda et al. (1994) "KF 17837: a novel selective adenosine A$_{2A}$ receptor antagonist with anticataleptic activity" Eur. J. Pharmacol. 52:48-54

Kanda et al. (1998a) "Adenosine A$_{2A}$ antagonist: a novel antiparkinsonian agent that does not provoke dyskinesia in parkinsonian monkeys" Ann. Neurol. 43:507-513

Kanda et al. (1998b) NeuroReport 9:2857-2860

Kanda et al. (2000) "Combined use of the adenosine A$_{2A}$ antagonist KW-6002 with L-DOPA or with selective D$_1$ or D$_2$ dopamine agonists increases antiparkinsonian activity but not dyskinesia in MPTP-treated monkeys" Exp. Neurol. 162:321-327

Karp et al. (1981) "Metoclopramide treatment of tardive dyskinesia" JAMA 246:1934-1935

Kase et al. (2000) "Adenosine receptors and Parkinson's disease" Academic Press, San Diego Kase (2001) "New aspects of physiological and pathophysiological functions of adenosine A$_{2A}$ receptor in basal ganglia" Biosci. Biotechnol. Biochem. 65:1447-1457

Kawaguchi (1989) "Intracellular recording of identified neostriatal patch and matrix spiny cells in a slice preparation preserving cortical inputs" J. Neurophysiol. 62:1052-1068

Kawaguchi et al. (1990) "Projection subtypes of rat neostriatal matrix cells revealed by intracellular injection of biocytin" J. Neurosci. 10:3421-3438

Kawaguchi et al. (1995) "Striatal interneurons: chemical, physiological and morphological characterization" Trends Neurosci. 18:527-535

Kawaguchi (1997) "Neostriatal cell subtypes and their functional roles" Neurosci. Res. 27:1-8

Kirk et al. (1994) "Adenosine A$_{2A}$ receptor-mediated modulation of striatal [$^3$H]GABA and [$^3$H]acetylcholine release" J. Neurochem. 62:960-966

Kita et al. (1983) "Pallidal inputs to subthalamus: intracellular analysis" Brain Res. 264:255-265

Kita (1993) "GABAergic circuits of the striatum" in: Arbuthnott et al. eds., Progress in Brain Research, Elsevier Science Publishers B.V. 99:51-72

Kita (1994) "Parvalbumin-immunopositive neurons in rat globus pallidus: a light and electron microscope study" Brain Res. 657:31-41

Kita (1996) "Glutamatergic and GABAergic postsynaptic responses of striatal spiny neurons to intrastriatal and cortical stimulation recorded in slice preparations" Neurosci. 70:925-940

Klawans et al. (1980) "Tardive dyskinesia: Review and update" Am. J. Psych. 137:900-908

Koga et al. (2000) "Adenosine A$_{2A}$ receptor antagonists KF17837 and KW-6002 potentiate rotation induced by dopaminergic drugs in hemi-parkinsonian rats" Eur. J. Pharmacol. 408:249-255

Koos (1999) "Inhibitory control of neurostriatal projection neurons by GABAergic interneurons" Nature Neurosci. 2:467-472

Kurokawa et al. (1994) "Inhibition by KF17837 of adenosine A$_{2A}$ receptor-mediated modulation of striatal GABA and Ach release" BR. J. Pharmacol. 113:43-48

Kurokawa et al. (1996) J. Neurochem. 66:1882-1888

Kuwana et al. (1999) Adv. Neurol. 80:121-123

Lindroth and Mopper (1979) "High performance liquid chromatography determination of subpicomole amounts of amino acids by precolumn fluorescence derivatization with o-phthaldialdehyde" Analyt. Chem. 51:1667-1674

Lohr and Caligiuri (1996) "A double-blind placebo-controlled study of vitamin E treatment of tardive dyskinesia" J. Clin. Psych. 57:167-73

Lohr et al. (1988) "Vitamin E in the treatment of tardive dyskinesia: the possible involvement of free radical mechanisms" Schiz. Bull. 14:291-296

Loopuijt et al. (1985) "Organization of the striatum: collateralization of its efferent axons" Brain Res. 348:86-99

Marsden et al. (1982) "Fluctuations in disability in Parkinson's disease: clinical aspects" In: Mardsen, C D, Fahn S., eds. Movement disorders. New York: Butterworth Scientific pp. 96-122

McCreadie et al. (1994) "The Nithsdale Schizophrenia Surveys. XIV: Plasma lipid peroxide and serum vitamin E levels in patients with and without tardive dyskinesia, and in normal subjects" Am. J. Psych. 151:925-926

Moore and Bowers (1980) "Identification of a subgroup of tardive dyskinesia patients by pharmacologic probes" Am. J. Psych. 137:1202-1205

Mori et al. (1996) "The role of adenosine $A_{2A}$ receptors in regulating GABAergic synaptic transmission in striatal medium spiny neurons" J. Neurosci. 16:605-611

Mori et al. (2002) "Adenosine $A_{2A}$ receptor-mediated dual modulation of GABAergic synaptic transmission in the striatopallidal system and its implication in action mechanism of $A_{2A}$ antagonists for a novel therapy in Parkinson's disease" Neurol. (in press)

Moss et al. (1993) "Buspirone in the treatment of tardive dyskinesia" J. Clin. Psychopharmacol. 13:204-209

Nakanishi et al. (1987) "Electrical membrane properties of rat subthalamic neurons in an in vivo slice preparation" Brain Res. 437:35-44

Nambu et al. (1997) "Morphology of globus pallidus neurons: its correlation with electrophysiology in guinea pig brain slices" J. Comp. Neurol. 377:85-94

Nonaka et al. (1994) "(E)-8-(3,4,5-trimethoxystyryl)-1,3-dipropyl-7-methyl-xanthine, a potent and selective adenosine $A_{2A}$ receptor antagonist" Eur. J. Pharmacol. 267:335-341

Nonaka et al. (2002) "Biochemical characterization of a novel adenosine $A_{2A}$ receptor antagonist, KW-6002" Seikaguku 74:937 3P663 (Abstract)

Obeso et al. (1997) "Basal ganglia physiology—A critical review" Advances in Neurology (Obeso et al. eds) 74:3-7 Lippincott Raven Publishers, Philadelphia Obeso et al. (2000) "Pathophysiology of the basal ganglia in Parkinson's disease" Trends Neurosci. 23(Suppl):S8-S19

Ochi et al. (2000) "Systemic adenosine $A_{2A}$ receptor antagonist decreases GABA release from rat globus pallidus increased by nigrostriatal lesions: A microdialysis study" Neuroscience 100:53-62

Oertel et al. (1984) "Immunocytochemical studies of GABAergic neurons in rat basal ganglia and their relations to other neuronal systems" Neurosci. Lett. 47:233-238

Olanow, Watts and Koller eds.(2001) An Algorithm (Decision Tree) for the Management of Parkinson's Disease (2001): Treatment Guidelines, Neurology 56, Suppl. 5.

Parkinson Study Group (1996) "Impact of deprenyl and tocopherol treatment on Parkinson's disease in DATATOP patients requiring levodopa" Ann. Neurol. 39:37-45

Parkinson Study Group (2000) "Pramipexole vs. levodopa as initial treatment for Parkinson's disease: a randomized controlled trial" JAMA 284:1931-1938

Paskevich et al. (1991) "Morphological assessment of neuronal aggregates in the striatum of the rat" J. Comp. Neurol. 305:361-369

Przedborski et al. (1995) Neuroscience 67:631-647

Rascol et al. (2000) "A five-year study of the incidence of dyskinesia in patients with early Parkinson's disease who were treated with ropinirole or levodopa" N. Eng. J. Med. 342:1484-1491

Richardson et al. (1997) "Adenosine $A_{2A}$ receptor antagonists as new agents for the treatment of Parkinson's disease" Trends Pharmacol. Sci. 18:338-344

Rosin et al. (1998) "Immunohistochemical localization of adenosine $A_{2A}$ receptors in the rat central nervous system" J. Comp. Neurol. 401:163-186

Schiffmann et al. (1990) Brain Res. 519:333-337

Schiffmann et al. (1991a) "Striatal restricted $A_2$ receptor (RDC8) is expressed by enkephalin but not by substance P neurons: an in situ hybridization histochemistry study" J. Neurochem. 57:1062-1067

Schiffmann et al. (1991 b) "Distribution of adenosine $A_2$ receptor mRNA in the human brain" Neurosci. Lett. 130:177-181

Sherzai et al. (2002a) "Adenosine $A_{2A}$ antagonist treatment of Parkinson's disease" Neurol. 54(Suppl 6):P06.104

Sherzai et al. (2002b) "Adenosine $A_{2A}$ antagonist treatment of Parkinson's disease" Neurol. 58(suppl 3):A467

Shimada et al. (1992) "(E)-1,3-dialkyl-7-methyl-8-(3,4,5-trimethoxystyryl)xanthines: potent and selective adenosine $A_2$ antagonists" J. Med. Chem. 35:2342-2345

Shimada et al. (1997) "Adenosine $A_{2A}$ antagonists with potent anti-cataleptic activity" Bio. Med. Chem. Lett. 7:2349-2352

Shindou et al. (2001) "Adenosine $A_{2A}$ receptor enhances $GABA_A$-mediated IPSCs in the rat globus pallidus" J. Physiol. 532:423-434

Shindou et al. (2002) "Presynaptic adenosine $A_{2A}$ receptor enhances GABAergic synaptic transmission via cAMP dependent mechanism in the rat globus pallidus" Br. J. Pharmacol. 136:296-302

Shiozaki et al. (1999) "Action of adenosine $A_{2A}$ receptor antagonist KW-6002 on drug-induced catalepsy and hypokinesia caused by reserpine or MPTP" Psychopharmacology 147:90-95

Shiriqui et al. (1992) "Vitamin E in the treatment of tardive dyskinesia: a double-blind placebo-controlled study" Am. J. Psych. 149:391-143

Shulman and Weiner (1997) Multiple system atrophy. In: Watts and Koller eds. Movement Disorders: Neurological Principles and Practice. New York, N.Y.: McGraw-Hill pp. 297-306

Smith et al. (1987) "Distribution of GABA-immunoreactive neurons in the basal ganglia of the squirrel monkey" J. Comp. Neurol. 259:50-64

Stern et al. (1998) "Membrane potential synchrony of simultaneously recorded striatal spiny neurons in vivo" Nature 394:475-478

Tepper and Haas (1979) "Prevalence of tardive dyskinesia" J. Clin. Psych. 40:508-516

Thaker et al. (1990) "Clonazepam treatment of tardive dyskinesia: a practical GABAmimetic strategy" Am. J. Psych. 147:445-451

Uhrbrand and Faurbye (1960) "Reversible and irreversible dyskinesia after treatment with perphenazine, chlorpromazine, reserpine, ECT therapy" Psychopharmacologia 1:408-418

Watts and William eds. (1997) Movement Disorders: Neurologic Principles and Practice. New York: McGraw-Hill Wichmann et al. (1993) "Pathophysiology of parkinsonian motor abnormalities" In: Narabayashi et al. eds. Advance in Neurology, Raven Press Ltd., 60:53-61

Wilbur and Kulik (1980) "Propranolol for tardive dyskinesia and EPS from neuroleptics: Possible involvement of β-adrenergic mechanisms" Prog. Neuro-Psychopharmacol. 4:627-632

What is claimed is:

1. A method of prolonging effective treatment of Parkinson's disease, comprising administering to a patient in need thereof (E)-8-(3,4-dimethoxystyryl)-1,3-diethyl-7-methylxanthine, in an amount effective to delay the patient's need for add-on L-DOPA therapy, wherein the patient currently receives L-DOPA therapy.

2. The method according to claim 1 wherein the development of motor complications is delayed.

3. The method according to claim 1 wherein the patient does not have subsequent administration of L-DOPA.

* * * * *